US008365065B2

(12) United States Patent
Gejdos et al.

(10) Patent No.: US 8,365,065 B2
(45) Date of Patent: Jan. 29, 2013

(54) METHOD AND SYSTEM FOR CREATING USER-DEFINED OUTPUTS

(75) Inventors: Igor Gejdos, Indianapolis, IN (US); Morris J. Young, Indianapolis, IN (US); Jason Bush, Fishers, IN (US); Scott W. Leahy, Fort Wayne, IN (US); Schuyler Buck, Muncie, IN (US); Ryan Scott McKinney, Jamestown, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1097 days.

(21) Appl. No.: 11/999,905

(22) Filed: Dec. 7, 2007

(65) Prior Publication Data
US 2009/0150758 A1 Jun. 11, 2009

(51) Int. Cl.
*G06F 17/27* (2006.01)
(52) U.S. Cl. ......... 715/215; 715/221; 715/222; 715/235
(58) Field of Classification Search .................. 715/215, 715/221, 222, 235
See application file for complete search history.

(56) References Cited

U.S. PATENT DOCUMENTS

| | | | |
|---|---|---|---|
| 5,251,126 A | 10/1993 | Kahn et al. | |
| 5,497,486 A | 3/1996 | Stolfo et al. | |
| 5,581,460 A * | 12/1996 | Kotake et al. | 705/3 |
| 5,671,404 A | 9/1997 | Lizee et al. | |
| 5,671,409 A | 9/1997 | Fatseas et al. | |
| 5,847,706 A * | 12/1998 | Kingsley | 715/788 |
| 5,860,073 A * | 1/1999 | Ferrel et al. | 715/255 |
| 5,894,311 A * | 4/1999 | Jackson | 345/440 |
| 5,941,820 A * | 8/1999 | Zimmerman | 600/300 |
| 5,960,403 A | 9/1999 | Brown | |
| 5,995,962 A | 11/1999 | Horowitz | |
| 6,004,276 A * | 12/1999 | Wright et al. | 600/508 |
| 6,004,944 A * | 12/1999 | Rothman et al. | 514/44 R |
| 6,024,699 A | 2/2000 | Surwit et al. | |
| 6,032,119 A | 2/2000 | Brown et al. | |
| 6,322,502 B1 | 11/2001 | Schoenberg et al. | |
| 6,425,863 B1 | 7/2002 | Werner et al. | |
| 6,505,980 B1 * | 1/2003 | Allday | 400/61 |
| 6,562,001 B2 | 5/2003 | Lebel et al. | |
| 6,564,105 B2 | 5/2003 | Starkweather et al. | |

(Continued)

FOREIGN PATENT DOCUMENTS

| | | |
|---|---|---|
| DE | 20217855 | 2/2003 |
| EP | 0970655 | 1/2000 |

(Continued)

OTHER PUBLICATIONS

Altova XMLSpy Professional Edition User Manual; 2006; Altova; pp. 19, 73, 77-78, 155, and 472-474.*

(Continued)

*Primary Examiner* — Doug Hutton, Jr.
*Assistant Examiner* — Andrew Dyer
(74) *Attorney, Agent, or Firm* — Faegre Baker Daniels LLP

(57) ABSTRACT

A system and method for creating a template configured to generate reports for reporting medical information. The method allows a user to generate a single template that may be then utilized in order to create a plurality of reports for numerous patients. The template is created by dragging and dropping the desired information onto a blank report. Once the desired format of the template has been set by the user, the user may save the template for future use.

21 Claims, 42 Drawing Sheets

U.S. PATENT DOCUMENTS

| | | | |
|---|---|---|---|
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,605,038 B1 | 8/2003 | Teller et al. | |
| 6,635,014 B2 | 10/2003 | Starkweather et al. | |
| 6,648,821 B2 | 11/2003 | Lebel et al. | |
| 6,659,948 B2 | 12/2003 | Lebel et al. | |
| 6,668,196 B1 | 12/2003 | Villegas et al. | |
| 6,668,354 B1* | 12/2003 | Chen et al. | 715/255 |
| 6,687,546 B2 | 2/2004 | Lebel et al. | |
| 6,694,191 B2 | 2/2004 | Starkweather et al. | |
| 6,733,446 B2 | 5/2004 | Lebel et al. | |
| 6,740,075 B2 | 5/2004 | Lebel et al. | |
| 6,758,810 B2 | 7/2004 | Lebel et al. | |
| 6,781,522 B2 | 8/2004 | Sleva et al. | |
| 6,804,656 B1 | 10/2004 | Rosenfeld et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,852,104 B2 | 2/2005 | Blomquist | |
| 6,873,268 B2 | 3/2005 | Lebel et al. | |
| 6,873,807 B2 | 3/2005 | Umetsu | |
| 6,958,705 B2 | 10/2005 | Lebel et al. | |
| 7,020,508 B2 | 3/2006 | Stivoric et al. | |
| 7,024,236 B2 | 4/2006 | Ford et al. | |
| 7,029,455 B2 | 4/2006 | Flaherty | |
| 7,041,468 B2 | 5/2006 | Drucker et al. | |
| 7,050,735 B2 | 5/2006 | Bardolatzy et al. | |
| 7,063,665 B2 | 6/2006 | Hasegawa et al. | |
| 7,082,334 B2 | 7/2006 | Boute et al. | |
| 7,113,946 B2 | 9/2006 | Cosic | |
| 7,165,062 B2 | 1/2007 | O'Rourke | |
| 7,179,226 B2 | 2/2007 | Crothall et al. | |
| 7,207,009 B1 | 4/2007 | Aamodt et al. | |
| 2002/0016568 A1 | 2/2002 | Lebel et al. | |
| 2002/0029776 A1 | 3/2002 | Blomquist | |
| 2002/0059299 A1 | 5/2002 | Spaey | |
| 2002/0062373 A1* | 5/2002 | Skingle | 709/225 |
| 2002/0184043 A1* | 12/2002 | Lavorgna et al. | 705/1 |
| 2002/0193679 A1 | 12/2002 | Malave et al. | |
| 2003/0011646 A1 | 1/2003 | Levine et al. | |
| 2003/0065308 A1 | 4/2003 | Lebel et al. | |
| 2003/0065536 A1 | 4/2003 | Hansen et al. | |
| 2003/0069758 A1 | 4/2003 | Anderson et al. | |
| 2003/0098869 A1 | 5/2003 | Arnold et al. | |
| 2003/0105638 A1* | 6/2003 | Taira | 704/275 |
| 2003/0140044 A1 | 7/2003 | Mok et al. | |
| 2003/0163088 A1 | 8/2003 | Blomquist | |
| 2003/0199739 A1 | 10/2003 | Gordon et al. | |
| 2003/0237046 A1* | 12/2003 | Parker et al. | 715/513 |
| 2004/0015783 A1* | 1/2004 | Lennon et al. | 715/523 |
| 2004/0030987 A1 | 2/2004 | Manelli | |
| 2004/0038389 A1 | 2/2004 | Maus et al. | |
| 2004/0073464 A1 | 4/2004 | Huang | |
| 2004/0086314 A1 | 5/2004 | Chen et al. | |
| 2004/0111296 A1 | 6/2004 | Rosenfeld et al. | |
| 2004/0172284 A1 | 9/2004 | Sullivan et al. | |
| 2005/0004947 A1 | 1/2005 | Emlet et al. | |
| 2005/0010452 A1 | 1/2005 | Lusen | |
| 2005/0125744 A1* | 6/2005 | Hubbard et al. | 715/824 |
| 2005/0131738 A1* | 6/2005 | Morris | 705/2 |
| 2005/0159977 A1 | 7/2005 | Green et al. | |
| 2005/0182655 A1 | 8/2005 | Merzlak et al. | |
| 2005/0187794 A1 | 8/2005 | Kimak | |
| 2005/0192844 A1 | 9/2005 | Esler et al. | |
| 2005/0259945 A1 | 11/2005 | Splaver | |
| 2006/0004603 A1* | 1/2006 | Peterka et al. | 705/2 |
| 2006/0010014 A1 | 1/2006 | Brown | |
| 2006/0020491 A1 | 1/2006 | Mongeon et al. | |
| 2006/0025931 A1* | 2/2006 | Rosen et al. | 702/19 |
| 2006/0031094 A1 | 2/2006 | Cohen et al. | |
| 2006/0061780 A1* | 3/2006 | Chen et al. | 358/1.8 |
| 2006/0095298 A1 | 5/2006 | Bina | |
| 2006/0155581 A1 | 7/2006 | Eisenberger et al. | |
| 2006/0161460 A1 | 7/2006 | Smitherman et al. | |
| 2006/0178910 A1 | 8/2006 | Eisenberger et al. | |
| 2006/0184524 A1 | 8/2006 | Pollanz | |
| 2006/0224638 A1 | 10/2006 | Wald et al. | |
| 2006/0272652 A1 | 12/2006 | Stocker et al. | |
| 2007/0033074 A1 | 2/2007 | Nitzan et al. | |
| 2007/0048691 A1 | 3/2007 | Brown | |
| 2007/0055940 A1 | 3/2007 | Moore et al. | |
| 2007/0088525 A1 | 4/2007 | Fotiades et al. | |
| 2007/0089071 A1 | 4/2007 | Zinn et al. | |
| 2007/0156032 A1* | 7/2007 | Gordon et al. | 600/300 |
| 2007/0169021 A1* | 7/2007 | Huynh et al. | 717/136 |
| 2007/0179352 A1 | 8/2007 | Randlov et al. | |
| 2007/0179975 A1 | 8/2007 | The et al. | |
| 2007/0189590 A1 | 8/2007 | Fidrich et al. | |
| 2007/0203751 A1* | 8/2007 | Koblasz | 705/2 |
| 2007/0219432 A1 | 9/2007 | Thompson | |
| 2007/0232866 A1 | 10/2007 | Nephin et al. | |
| 2007/0276197 A1 | 11/2007 | Harmon | |

FOREIGN PATENT DOCUMENTS

| | | |
|---|---|---|
| EP | 0649316 | 12/2000 |
| JP | 04/145774 | 5/2004 |
| JP | 04/145775 | 5/2004 |
| JP | 04/145776 | 5/2004 |
| JP | 07/058685 | 3/2007 |
| WO | WO9609590 | 3/1996 |
| WO | WO0018449 | 4/2000 |
| WO | WO 00/72181 | 11/2000 |
| WO | WO0072181 | 11/2000 |
| WO | WO0174229 | 10/2001 |
| WO | WO0200111 | 1/2002 |
| WO | WO02078512 | 10/2002 |
| WO | WO03015838 | 2/2003 |
| WO | WO2005037095 | 4/2005 |
| WO | WO2005096206 | 10/2005 |
| WO | WO2006050485 | 5/2006 |
| WO | WO2007084502 | 7/2007 |
| WO | WO2007093482 | 8/2007 |

OTHER PUBLICATIONS

Person et al.; Special Edition Using Microsoft Word 97; Dec. 16, 1996; Que Publishing; pp. 457-476.*

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

* cited by examiner

METHOD AND SYSTEM FOR CREATING USER-DEFINED OUTPUTS

FIELD OF THE INVENTION

The present invention relates to systems and methods for reporting medical information. In particular, the present invention relates to systems and methods for generating customized reports and letters and for distributing the reports and letters by fax, e-mail, mail and other means. Concepts described below may be further explained in one of more of the co-filed patent applications entitled HELP UTILITY FUNCTIONALITY AND ARCHITECTURE Ser. No. 11/999,906, METHOD AND SYSTEM FOR GRAPHICALLY INDICATING MULTIPLE DATA VALUES Ser. No. 11/999,853, SYSTEM AND METHOD FOR DATABASE INTEGRITY CHECKING Ser. No. 11/999,856, METHOD AND SYSTEM FOR DATA SOURCE AND MODIFICATION TRACKING Ser. No. 11/999,888, PATIENT-CENTRIC HEALTHCARE INFORMATION MAINTENANCE Ser. No. 11/999,874, EXPORT FILE WITH MANIFEST FOR ENHANCED DATA TRANSFER Ser. No. 11/999,867, GRAPHIC ZOOM FUNCTIONALITY FOR A CUSTOM REPORT Ser. No. 11/999,932, METHOD AND SYSTEM FOR SELECTIVE MERGING OF PATIENT DATA Ser. No. 11/999,859, METHOD AND SYSTEM FOR PERSONAL MEDICAL DATA DATABASE MERGING Ser. No. 11/999,772, METHOD AND SYSTEM FOR WIRELESS DEVICE COMMUNICATION Ser. No. 11/999,879, METHOD AND SYSTEM FOR SETTING TIME BLOCKS Ser. No. 11/999,968, METHOD AND SYSTEM FOR ENHANCED DATA TRANSFER Ser. No. 11/999,867, COMMON DATA EXCHANGE FORMAT Ser. No. 11/999,968, METHOD OF CLONING SERVER INSTALLATION TO A NETWORK CLIENT Ser. No. 11/999,876, METHOD AND SYSTEM FOR QUERYING A DATABASE Ser. No. 11/999,912, METHOD AND SYSTEM FOR EVENT BASED DATA COMPARISON Ser. No. 11/999,921, DYNAMIC COMMUNICATION STACK Ser. No. 11/999,934, SYSTEM AND METHOD FOR REPORTING MEDICAL INFORMATION Ser. No. 11/999,878, METHOD AND SYSTEM FOR MERGING EXTENSIBLE DATA INTO A DATABASE USING GLOBALLY UNIQUE IDENTIFIERS Ser. No. 11/999,947, METHOD AND SYSTEM FOR ACTIVATING FEATURES AND FUNCTIONS OF A CONSOLIDATED SOFTWARE APPLICATION Ser. No. 11/999,880, METHOD AND SYSTEM FOR CONFIGURING A CONSOLIDATED SOFTWARE APPLICATION Ser. No. 11/999,894, METHOD AND SYSTEM FOR DATA SELECTION AND DISPLAY Ser. No. 11/999,896, METHOD AND SYSTEM FOR ASSOCIATING DATABASE CONTENT FOR SECURITY ENHANCEMENT Ser. No. 11/999,951, METHOD AND SYSTEM FOR CREATING REPORTS Ser. No. 11/999,851, DATA DRIVEN COMMUNICATION PROTOCOL GRAMMAR Ser. No. 11/999,770, HEALTHCARE MANAGEMENT SYSTEM HAVING IMPROVED PRINTING OF DISPLAY SCREEN INFORMATION Ser. No. 11/999,855, and METHOD AND SYSTEM FOR MULTI-DEVICE COMMUNICATION Ser. No. 11/999,866, the entire disclosures of which are hereby expressly incorporated herein by reference. It should be understood that the concepts described below may relate to diabetes management software systems for tracking and analyzing health data, such as, for example, the ACCU-CHEK® 360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics or divisions thereof.

BACKGROUND OF THE INVENTION

Various systems for storing and reporting medical information are known. For example, systems are known which allow a user to download medical data from a device, such as a blood glucose meter, to a database, such as a database stored on a personal computer. In some such systems, the data can be displayed on monitor or printed.

SUMMARY OF THE INVENTION

Embodiments of the invention relate to a method of creating a template for reporting information. The method comprises the steps of displaying a plurality of content items on a first portion of a display; providing a template section on a second portion of the display; and placing at least one of the content items on the template section at a desired location.

In embodiments of the invention, the step of placing at least one of the content items includes the steps of dragging the at least one of the content items from the first portion of the display to the second portion of the display; and dropping the at least one of the content items at the desired location on the template section.

In embodiments of the invention, the at least one content item includes a graph. The method may include the step of altering the size of the graph. The step of altering the size of the graph may occur after the step of placing the graph in the template section. The method may further include the step of changing the scale of at least one of an x-axis or a y-axis as the size of the graph is altered. The scale of both the x-axis and the y-axis may change as the size of the graph is altered. Embodiments of the invention include the step of selecting the information displayed on the graph.

Embodiments of the invention include the step of displaying statistical information related to the graph. The at least one content item may include two graphs.

Embodiments of the invention include the step of saving the template in a database. The method may include the step of previewing the created template prior to saving the template. The method may further including the step of generating a report based upon the template. In embodiments of the invention, the report is a letter.

An embodiment of the invention is a method for creating a template capable of generating at least one report. The method may comprise the steps of providing a list including a plurality of content items; displaying a template section; and moving at least one of the content items from the list to a desired location in the template section.

BRIEF DESCRIPTION OF THE DRAWINGS

The above-mentioned and other features of this invention, and the manner of attaining them, will become more apparent and the invention itself will be better understood by reference to the following description of embodiments of the invention taken in conjunction with the accompanying drawings, wherein:

FIGS. 1 through 42 depict screen captures of software utilized in connection with embodiments of systems and methods for reporting medical information according to the present invention Although the drawings represent embodiments of various features and components according to the present invention, the drawings are not necessarily to scale and certain features may be exaggerated in order to better illustrate and explain the present invention. The exemplification set out herein illustrates certain embodiments of the invention, and such exemplification is not to be construed as limiting the scope of the invention in any manner.

DETAILED DESCRIPTION OF EMBODIMENTS OF THE INVENTION

Figure 1:
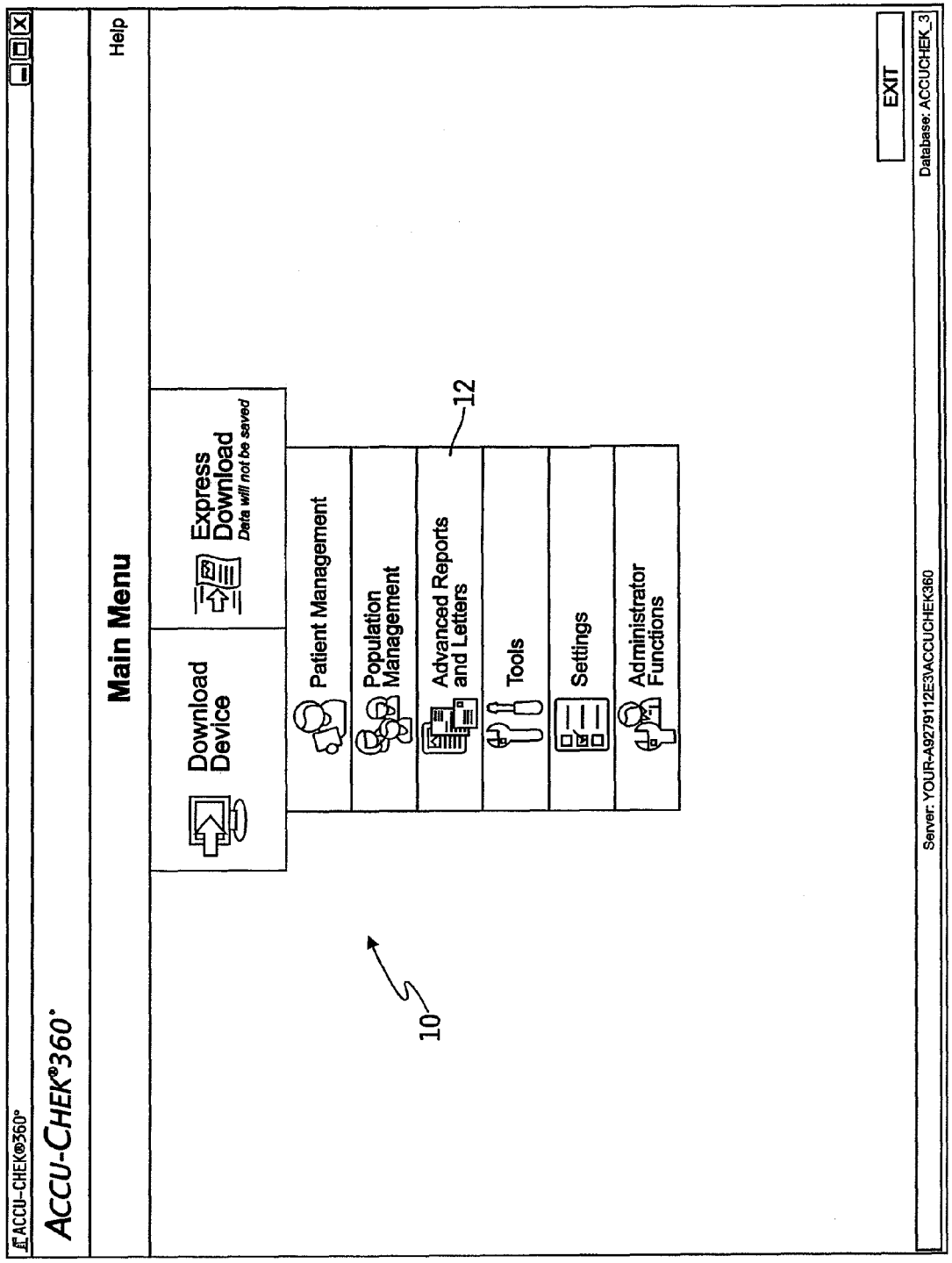

FIG. 1 is a screen capture of the main menu of a system for reporting medical information according to one embodiment of the present invention. As described in greater detail below, the system includes software having a database containing various letter templates, report templates, graphs, charts and data. The software may be installed and run on, for example, a personal computer.

Main menu 10 includes, among other icons, an icon 12 labeled "advanced reports and letters." The "advanced reports and letters" icon 12 can be selected by utilizing a mouse to position a cursor over icon 12 and clicking. Icon 12 can also be selected in other known manners.

Figure 2:
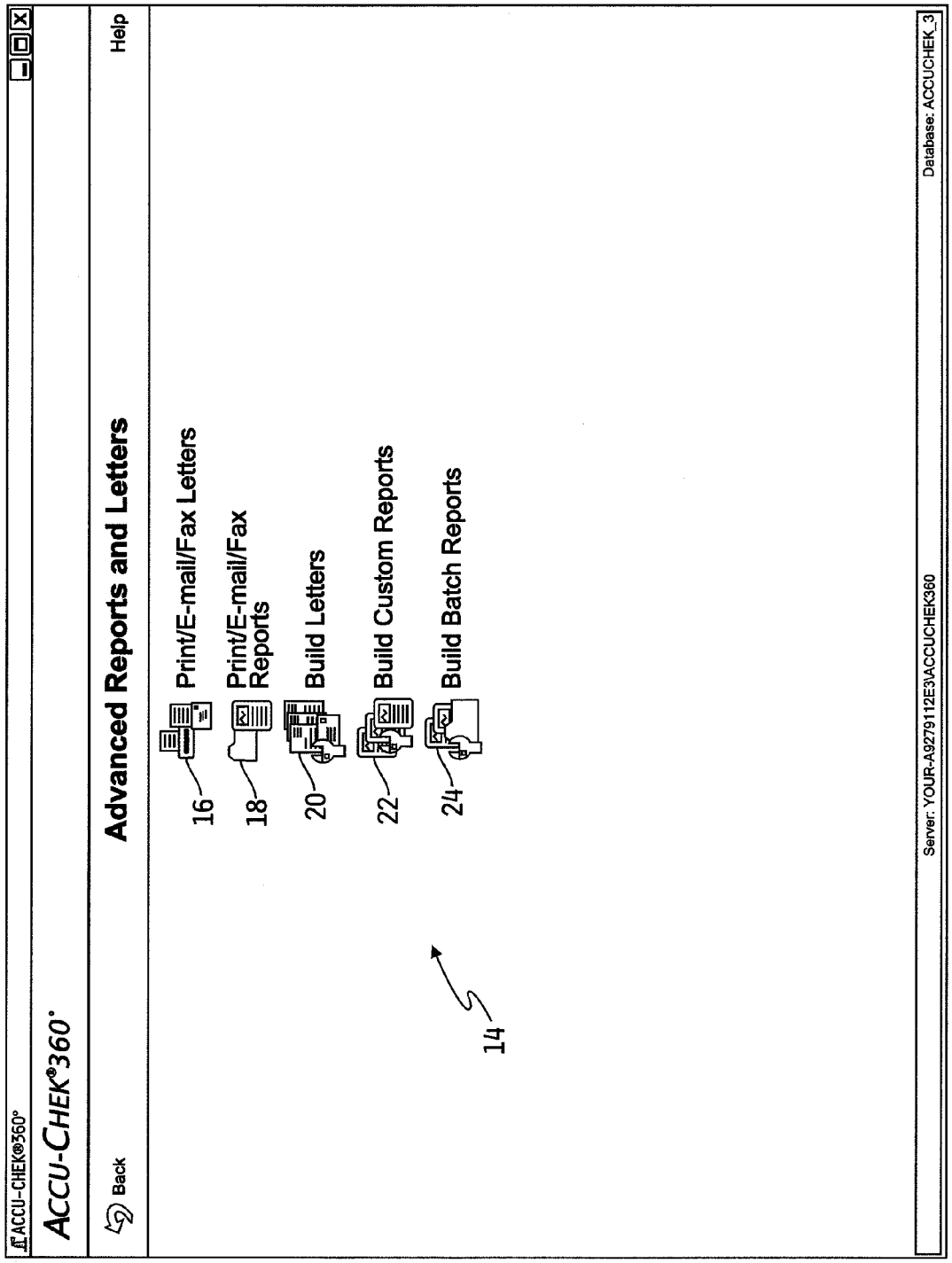

Selecting "advanced reports and letters" icon 12 displays "advanced reports and letters menu" 14 (FIG. 2). Menu 14 includes a "print/e-mail/fax letters" icon 16, a "print/e-mail/fax reports" icon 18, a "build letters" icon 20, a "build custom reports" icon 22 and a "build batch reports" icon 24. The "build letters" icon 20 and the "build custom reports" icon 22 allow the user to construct customized letter and report templates. The "build batch reports" icon 24 allows the user to construct batch reports that are a combination of predefined reports and letters stored in the system. The "print/e-mail/fax letters" icon 16 and "print/e-mail/fax reports" icon 18 allow the user to send reports via the various means indicated. These features are described in greater detail below.

Figure 3:
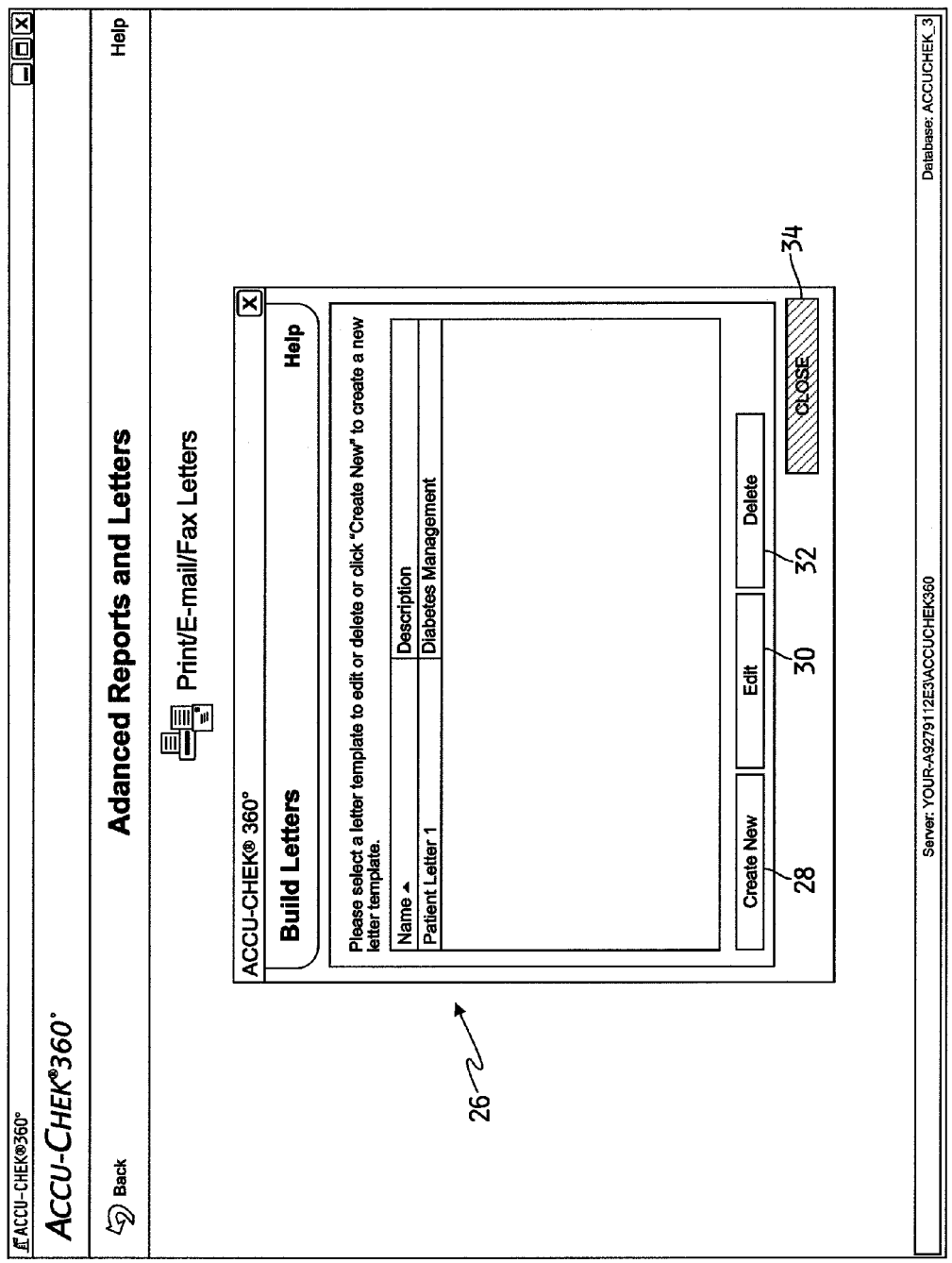

To create custom letter templates for reporting medical information, the user first selects the "build letters" icon 20. Selecting the "build letters" icon 20 displays a "letters menu" 26 that lists the available letters stored in the system (FIG. 3). "Letters menu" 26 includes a "create new" icon 28, an "edit" icon 30, a "delete" icon 32 and a "close" icon 34. In the embodiment shown, the "letters menu" 26 includes one stored letter template entitled "Patient Letter 1."

Figure 4:
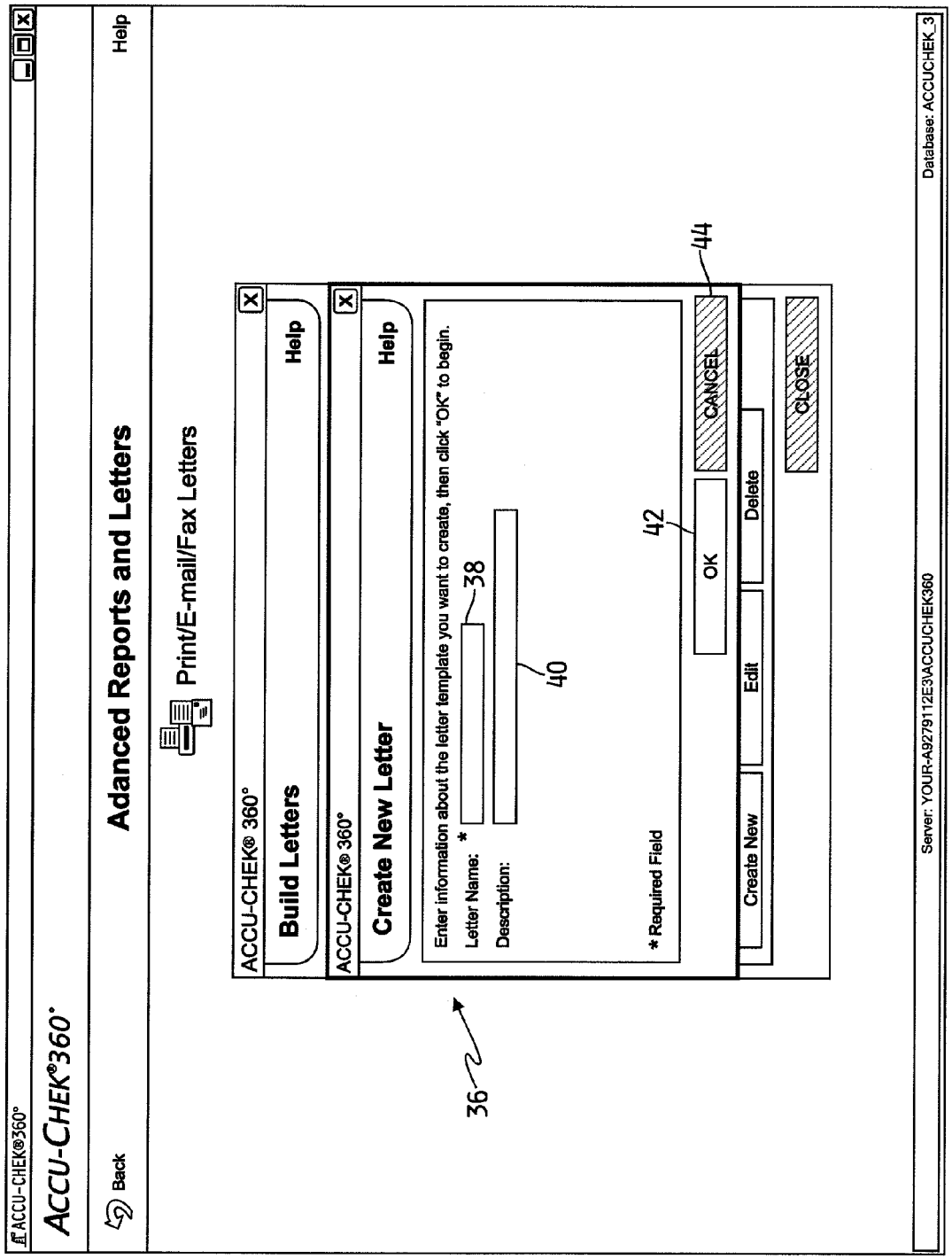
Figure 5:
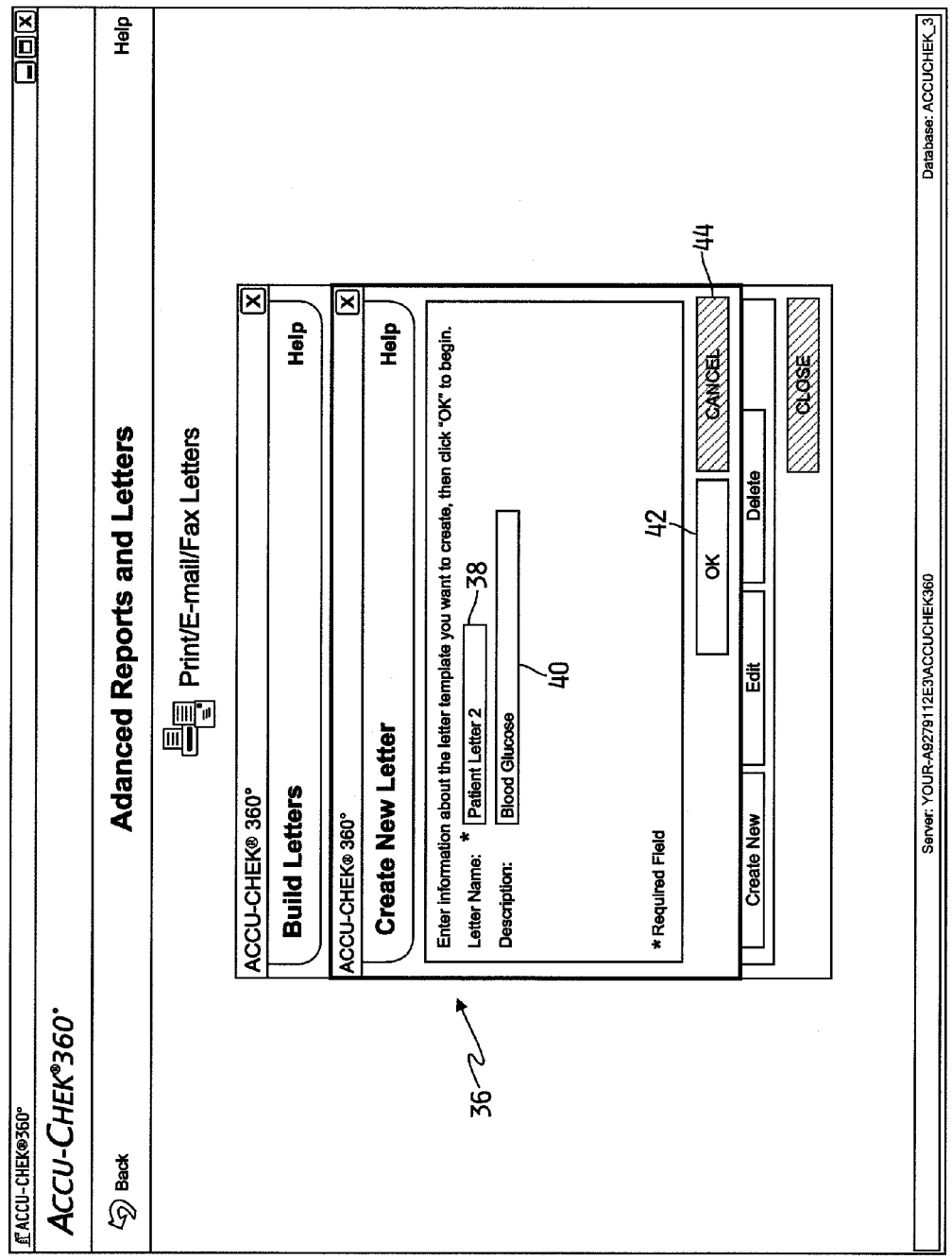

To create new letter templates, the user selects "create new" icon 28 which causes "create new letter" screen 36 to be displayed (FIG. 4). "Create new letter" screen 36 includes a text box 38 for entering the name of the new letter and a text box 40 for entering a description of the new letter. Entering text in boxes 38 and 40 causes "OK" icon 42 to become active (FIG. 5). "Create new letter" screen 36 further includes a "cancel" icon 44.

Figure 6:
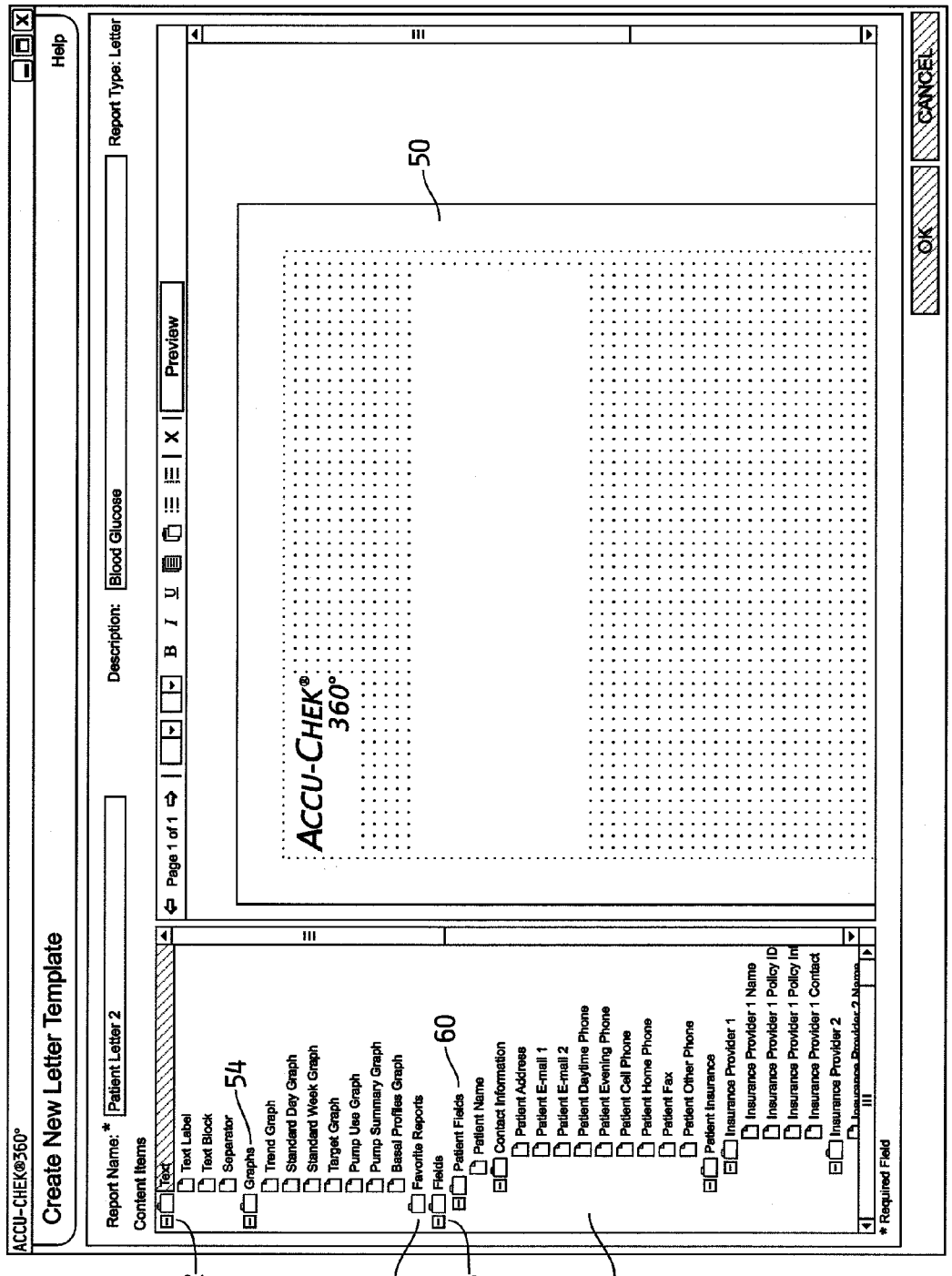
Figure 7:
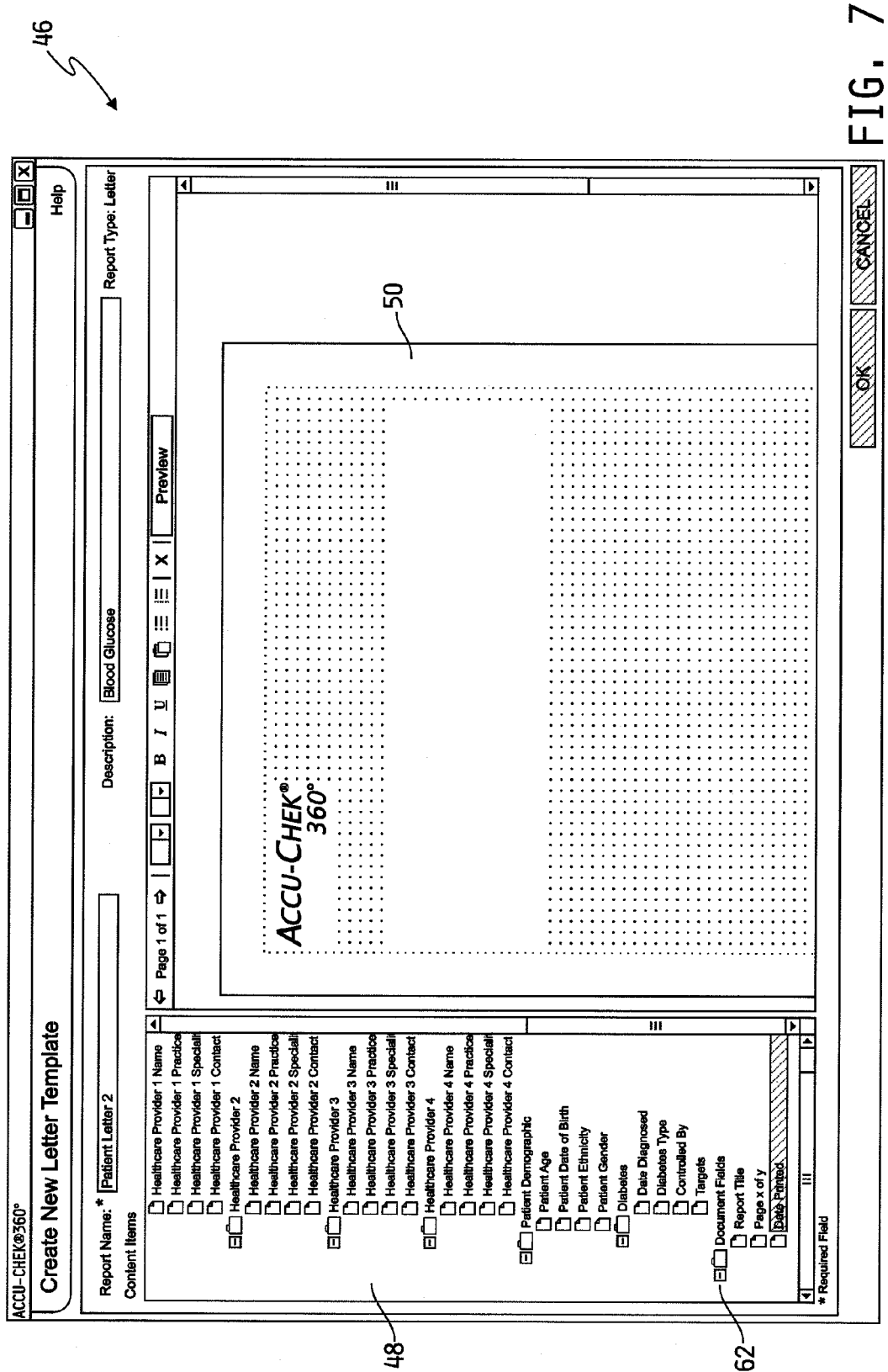

After entering the letter name and description, selecting "OK" icon 42 displays a "create new letter" template 46 (FIG. 6). Template 46 is generally divided into a first or content items section 48 and a second or template section 50. Content items section 48 includes a variety of content that can be utilized to create the letter template. For example, text content 52 includes various tools for placing written text in template section 50. Graphs content 54 includes various graphs stored in the system database that can be included in template section 50. Favorite reports content 56 includes the particular user's favorite or most frequently used reports. Fields content 58 includes patient content 60, which can include information such as (a) the patient's name, address, e-mail, phone numbers, fax numbers and other contact information, (b) insurance information including insurance provider, name, contact information and policy numbers, (c) patient healthcare provider information such as the healthcare provider's names, contact information and (d) patient demographic information such as the patient's age, birth date, ethnicity, gender and information regarding the patient's medical condition such as the date they were diagnosed with a particular disease (such as diabetes), the type of diabetes and other information. The document content 62 (FIG. 7) includes content that can be utilized in template section 50 to identify information about the document itself, such as its title, page numbers, the date the document was generated and other information.

The various content items may be stored in the system database in various forms. For example, blood glucose readings and other data for individual patients may be stored in the database and associated with the patient's name. Graph templates may be stored in the system database and populated with other stored data when the graph is generated for output as part of a report or letter, as described below.

Figure 8:
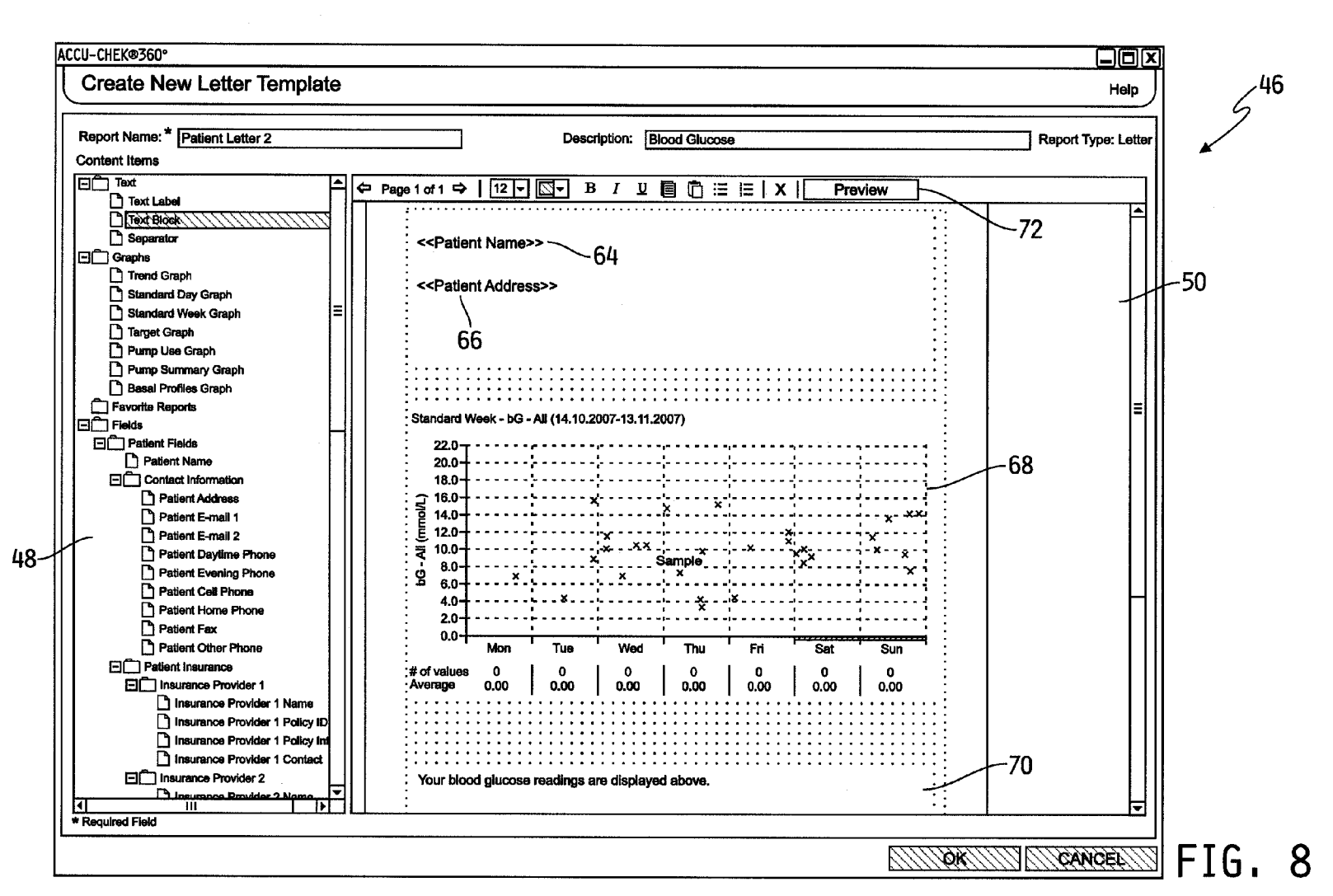
Figure 9:
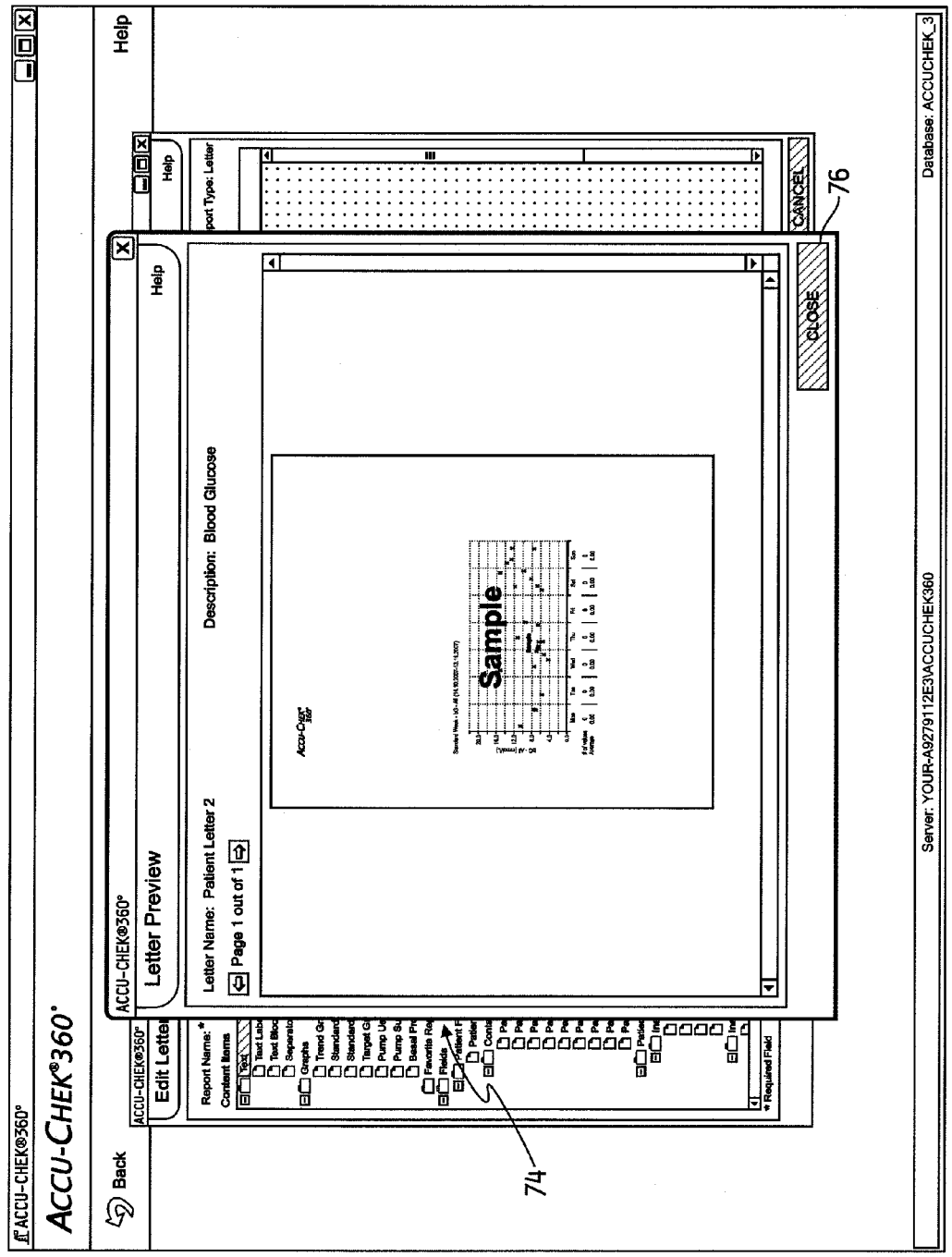

Letter templates can be generated by utilizing a mouse or other known hardware to drag and drop items from content items section 48 to template section 50. For example, in the template shown in FIG. 8, the patient name content 64 and patient address content 66 have been dragged and dropped from content section 48 to template section 50. The standard week graph 68 (which displays blood glucose measurements for a week) has also been dragged and dropped into template section 50. A text box 70 has also been dragged and dropped into the template section 50 and populated with the phrase "your blood glucose readings are displayed above." The user may, of course, select any desired combination of the content items for use in template section 50. If the user desires to preview the template prior to saving it, the user simply activates the "preview" icon 72. This causes a "letter preview" window 74 to be displayed which shows the format of the letter produced by the template (FIG. 9). To return to the "create new letter" template 46, the user simply selects the "close" icon 76.

Figure 10:
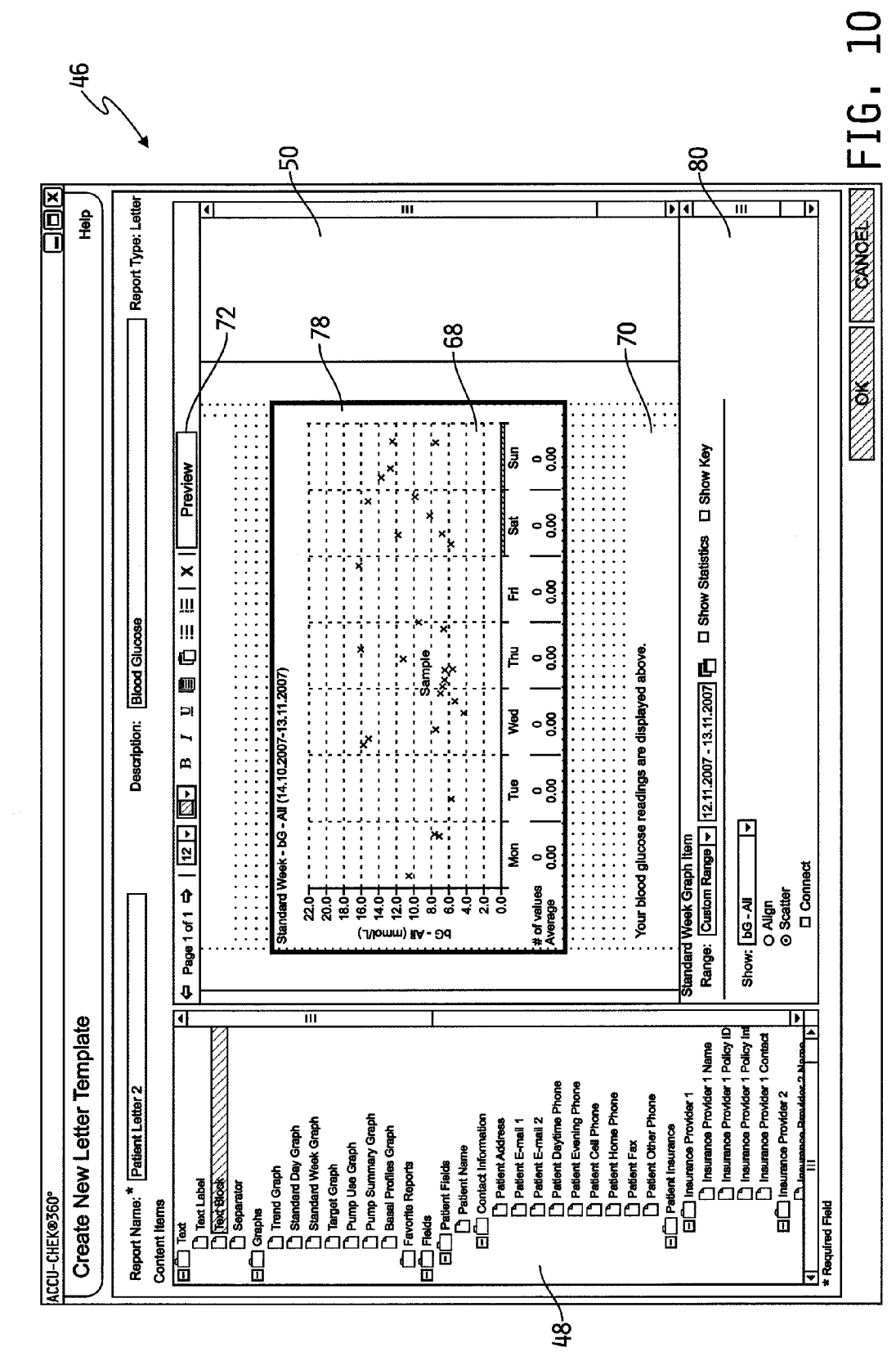
Figure 11:
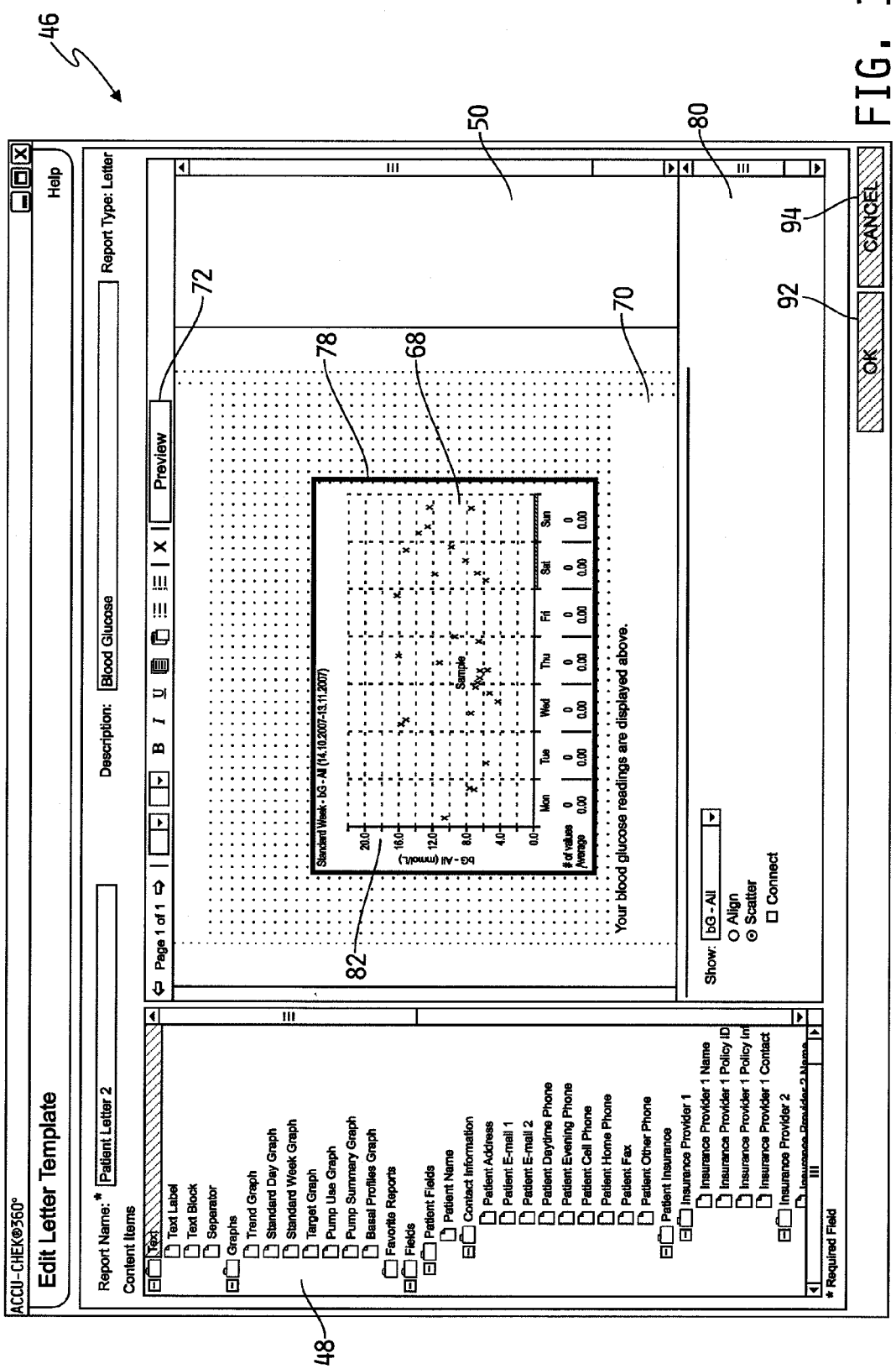

In one embodiment of the invention, the user can adjust the scale and content of the graphs and other information that have been dragged and dropped to template section 50. For example, if the user desires to alter the graph 68, he or she can position a cursor over the graph and click. This causes a boundary box 78 to be displayed around graph 68 and a "graph content" menu 80 to be displayed at the bottom of template section 50 (FIG. 10). The cursor can then be used to expand or contract boundary box 78 by positioning the cursor over a portion of the box and dragging it to increase or decrease the size, as is known in the art. For example, as shown in FIG. 11, boundary box 78 has been reduced in size, thereby reducing the size of graph 68. Note also that as graph 68 has been reduced in size, the y axis scale 82 has been relabeled to account for the change in the size. In FIG. 10, y axis scale 82 is marked in increments of 2 mmol/L, whereas in FIG. 11 it is marked in increments of 4 mmol/L. That is, adjusting boundary box 78 to adjust to size of graph 68 does not merely change the size of graph 68 but also reformats the x and y scales as needed.

Figure 12:
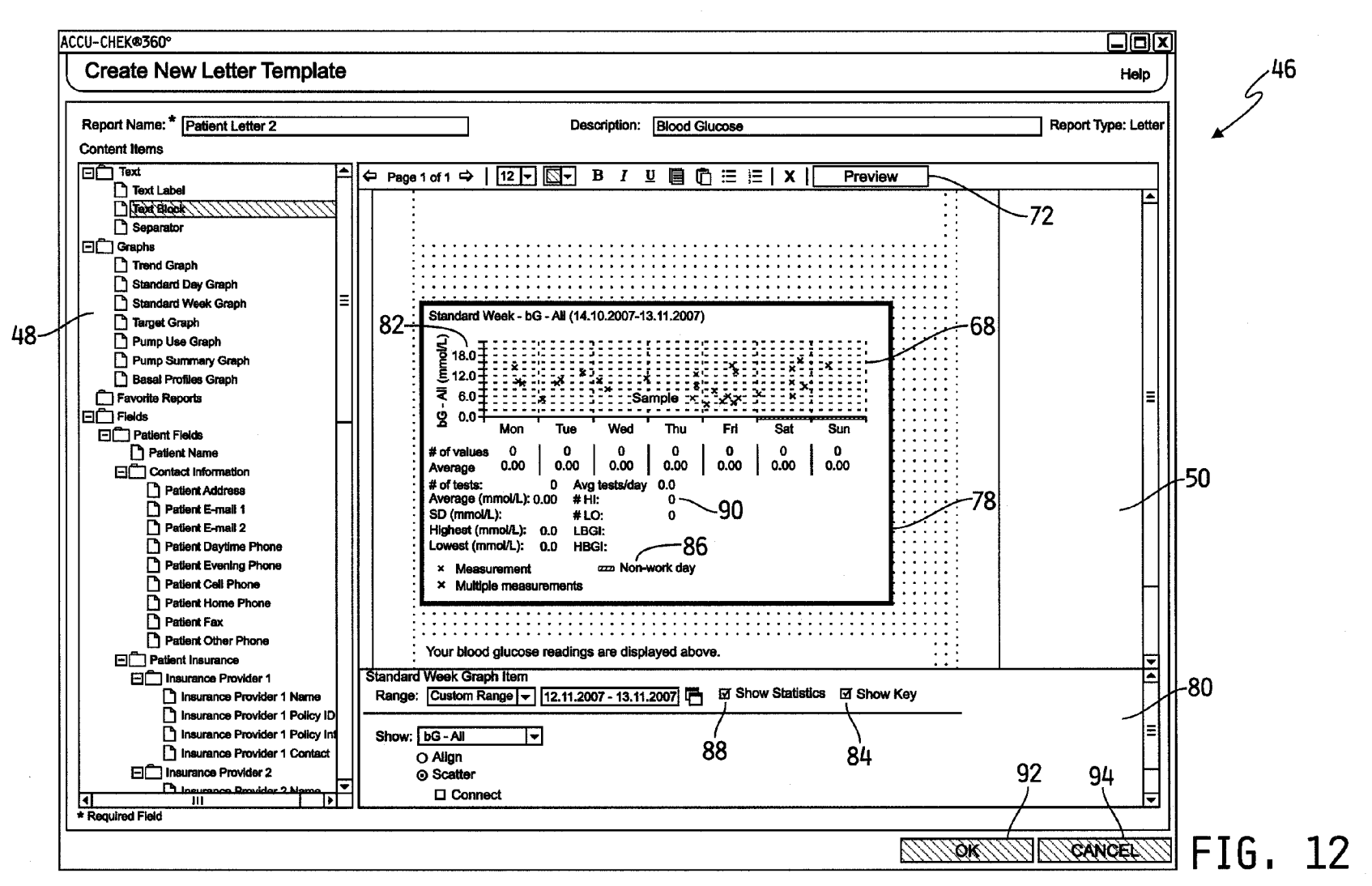

The present invention also allows the user to select desired content for graph 68 from the graph content menu 80. For example, if the user selects the "show key" box 84, the key 86 for reading graph 68 is displayed beneath it (FIG. 12). Note that the addition of key 86 has also caused y axis 82 to be further relabeled. Similarly, selecting the "show statistics" box 88 displays various statistics 90 in conjunction with graph 68. Clicking outside of boundary box 78 causes boundary box 78 and graph content menu 80 to disappear.

Figure 13:
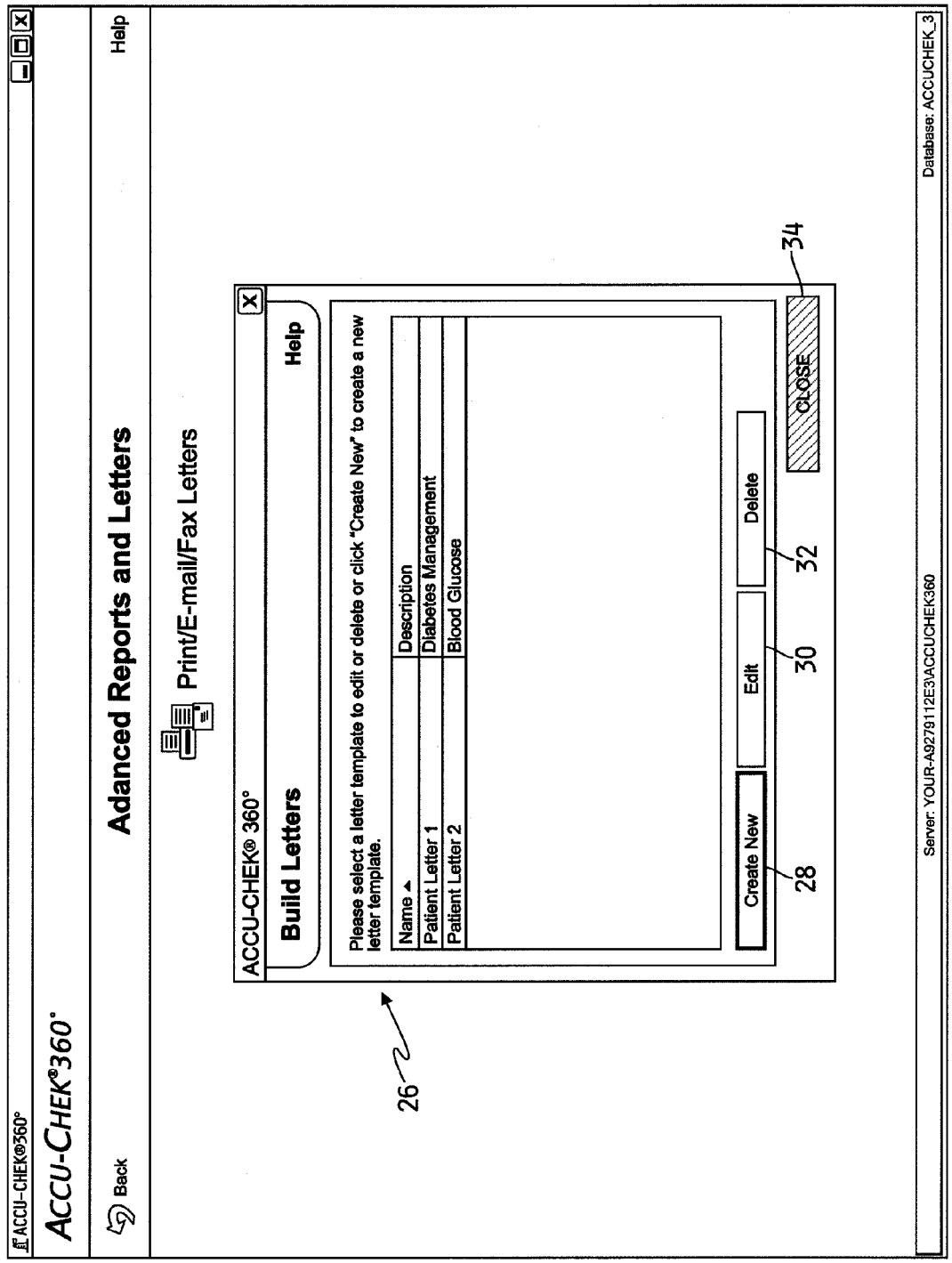

When the user is satisfied with the content of template section 50, he or she selects "OK" icon 92 to save the template in the system database with the previously stored letter and report templates. Selecting "OK" icon 92 also returns the user to "letters menu" 26 which now includes newly created Patient Letter 2 (FIG. 13). Alternatively, the user can select "cancel" icon 94 to abandon the operation and return to letters menu 26.

If the user wants to edit a template, he or she highlights the template to be edited and selects "edit" icon 30. This causes the stored template to be displayed with its content items section 48 and template section 50. The template can then be edited by dragging and dropping content, resizing graphs, changing text, etc. as described in connection with the method for creating the template. A stored letter template can be deleted by highlighting the template in menu 26 and selecting "delete" icon 32. Selecting "close" icon 34 returns the user to the "advanced reports and letters" menu 14.

Figure 14:
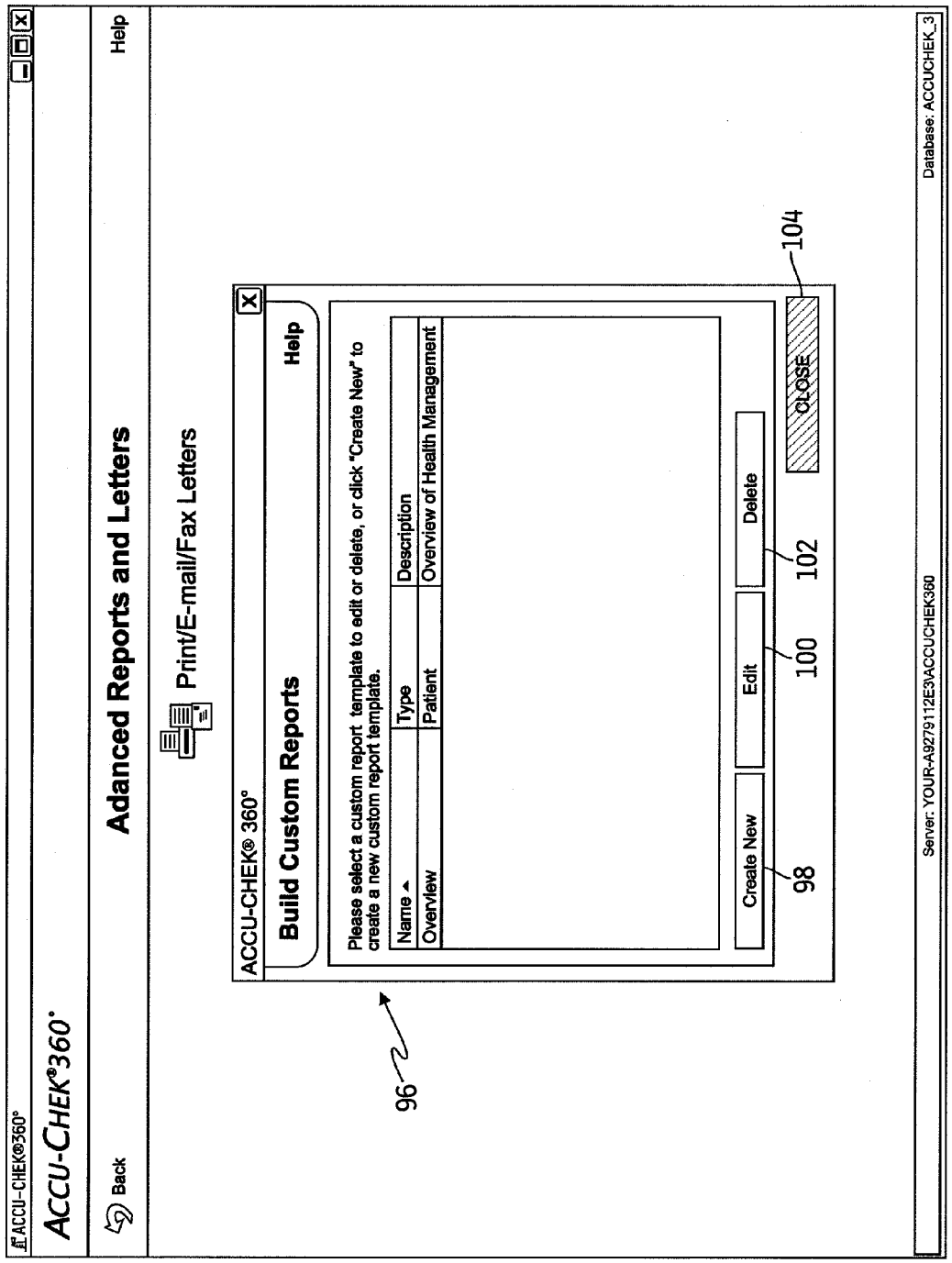

Returning to FIG. 2, selecting "build custom reports" icon 22 displays a "reports menu" 96 that lists the available reports stored in the system (FIG. 14). "Reports menu" 96 includes a "create new" icon 98, an "edit" icon 100, a "delete" icon 102 and a "close" icon 104. In the embodiment shown, the "reports menu" 96 includes one stored report template entitled "Overview."

Figure 15:
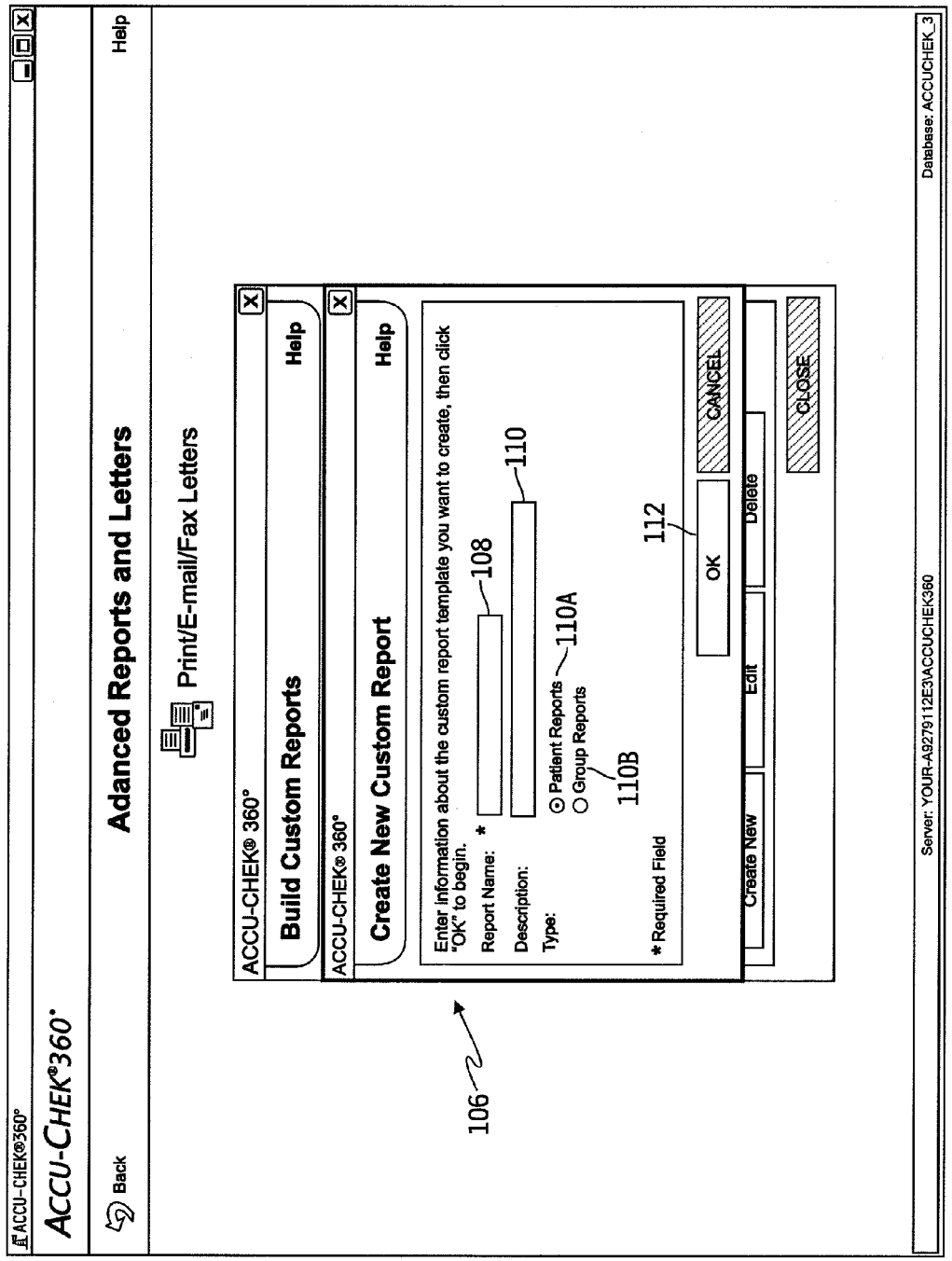
Figure 16:
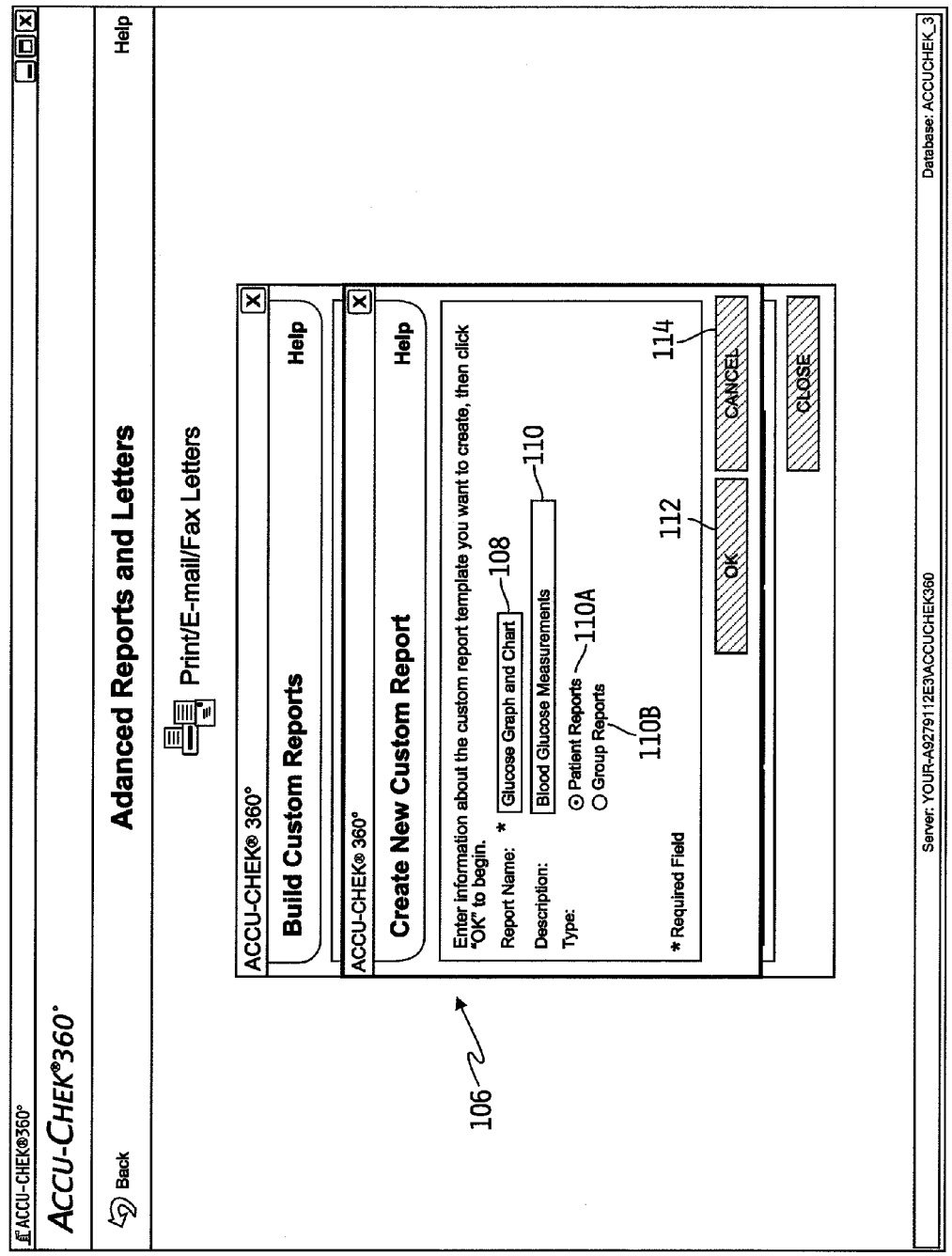

To create new report templates, the user selects "create new" icon 98 which causes "create new report" screen 106 to display (FIG. 15). "Create new report" screen 106 includes a text box 108 for entering the name of the new report and a text box 110 for entering a description of the new report. Entering text in boxes 108 and 110 causes "OK" icon 112 to become active (FIG. 16) "Create new report" screen 106 further includes a "cancel" icon 114. "Create new report" screen 106 also allows the user to define the report template type. In the example shown, the user can define the report as a patient report by selecting "patient report" option 110A or as a group report by selecting "group report" option 110B. In this manner, report templates can be created for reporting individual patient data or group patient data. For example, a user may want to create a report template for reporting data relating to a group of patients that are the same age, the same gender or that began a particular treatment at a particular time.

Figure 17:
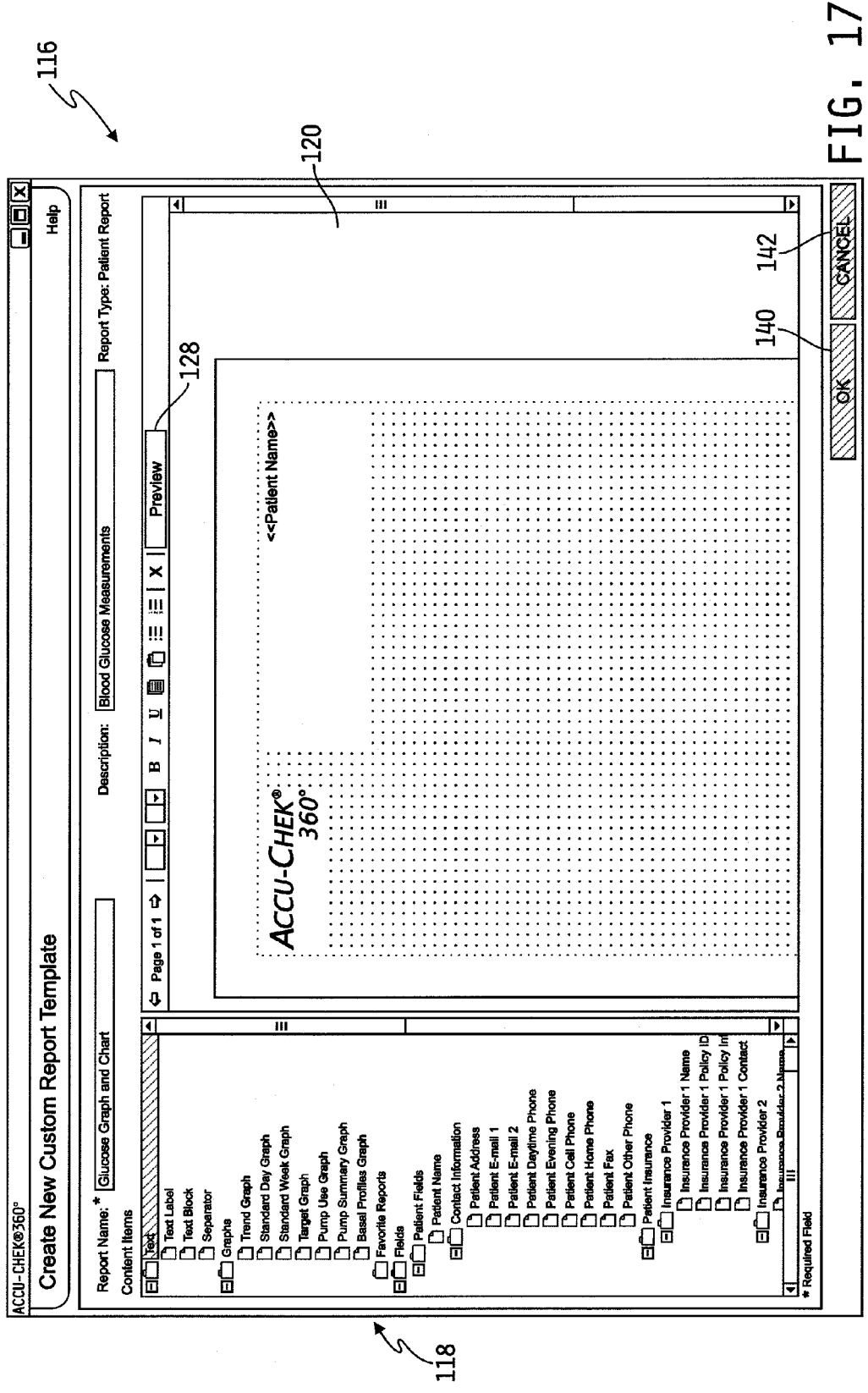

After entering the report name and description, selecting "OK" icon 112 displays a "create new report" template 116 (FIG. 17). Template 116 is generally divided into a first or content items section 118 and a second or template section 120. As with content section 48 described above, content items section 118 includes a variety of content that can be utilized to create the report template. This content can be the same as or different from the content in section 48.

Figure 18:
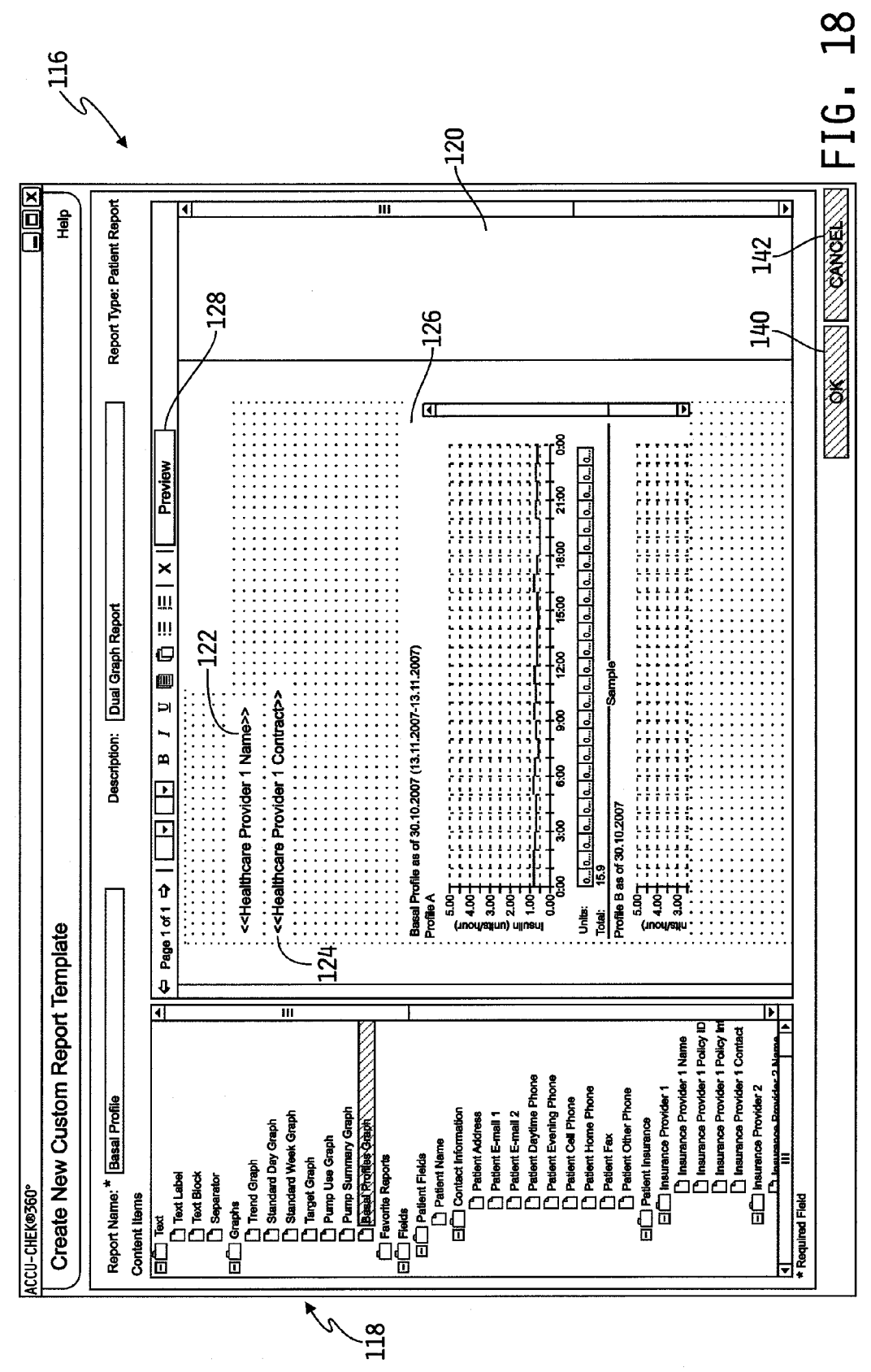
Figure 19:
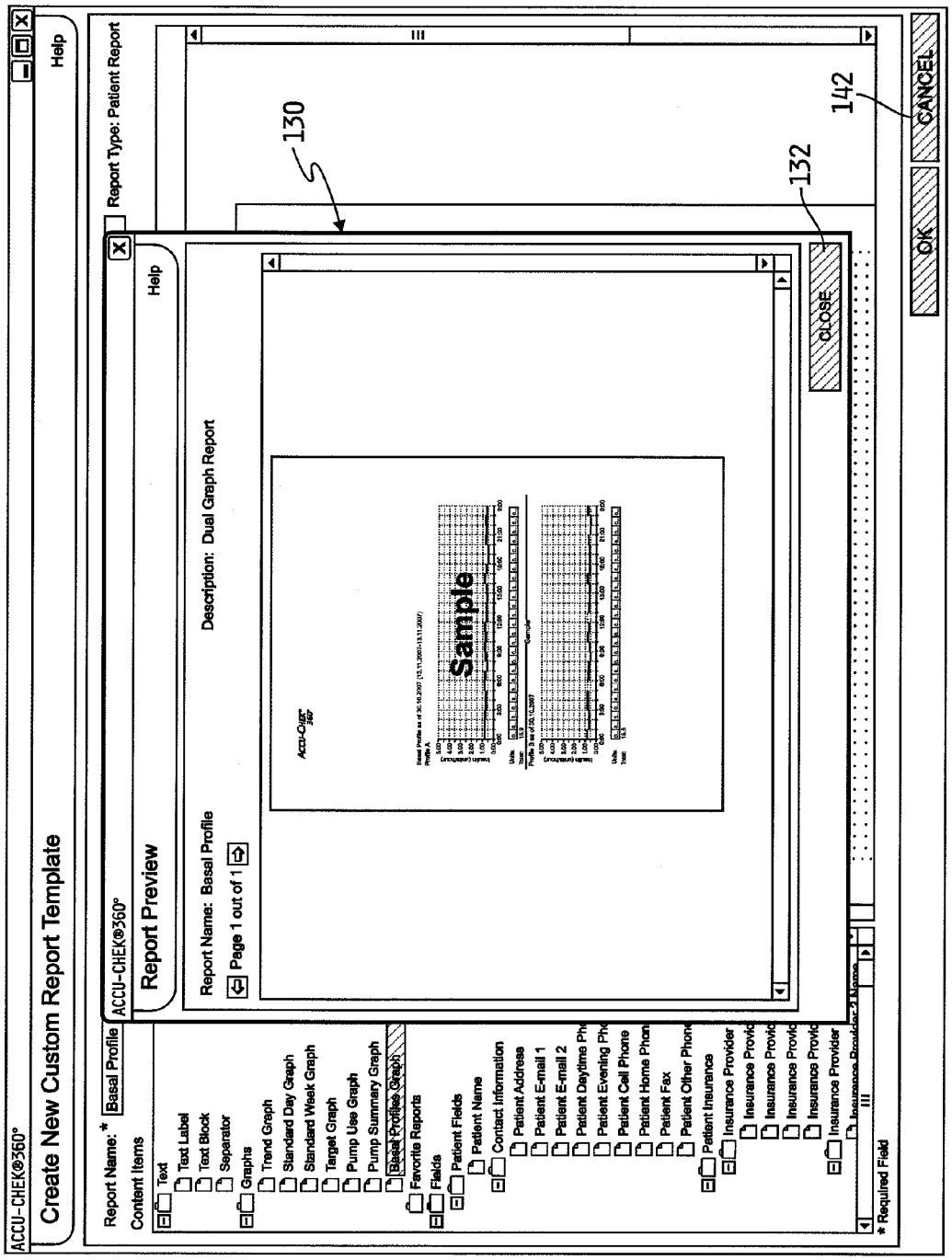

Report templates can be generated by utilizing a mouse or other known hardware to drag and drop items from content items section 118 to template section 120 in the same manner as described above with respect to "create new letter" template 46. For example, in the template shown in FIG. 18, the "healthcare provider 1 name" content 122 and "healthcare provider 1 contact" content 124 have been dragged and dropped from content items section 118 to template section 120. The basal profiles graph 126 (which displays information relating to insulin) has also been dragged and dropped into template section 120. As with building letters templates, the user may select any desired combination of the content items for use in template section 120. If the user desires to preview the template prior to saving it, the user simply activates the "preview" icon 128. This causes a "report preview" window 130 to be displayed which shows the format of the report produced by the template (FIG. 19). To return to the "create new report" template 116, the user simply selects the "close" icon 132.

Figure 20:
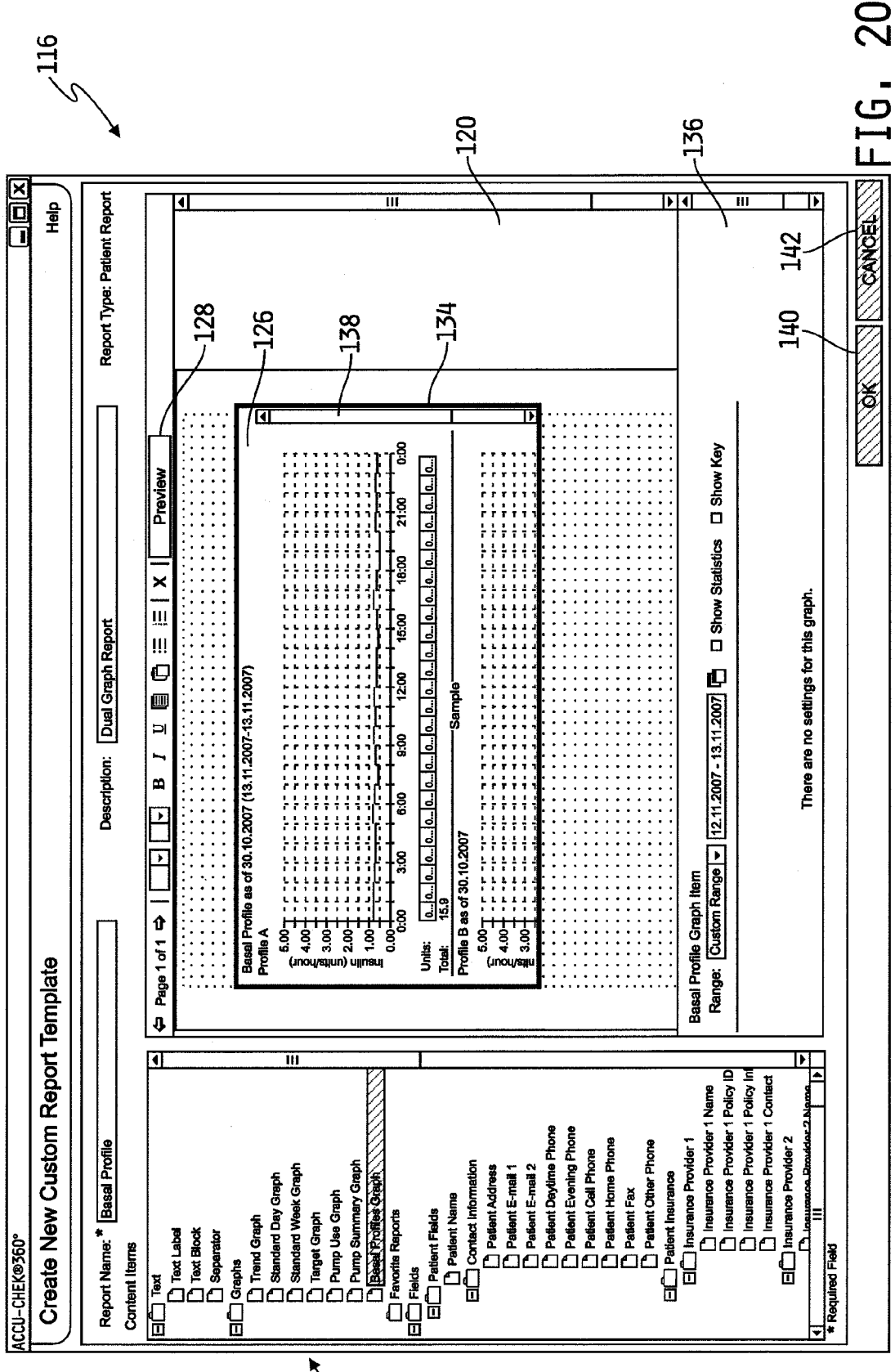
Figure 21:
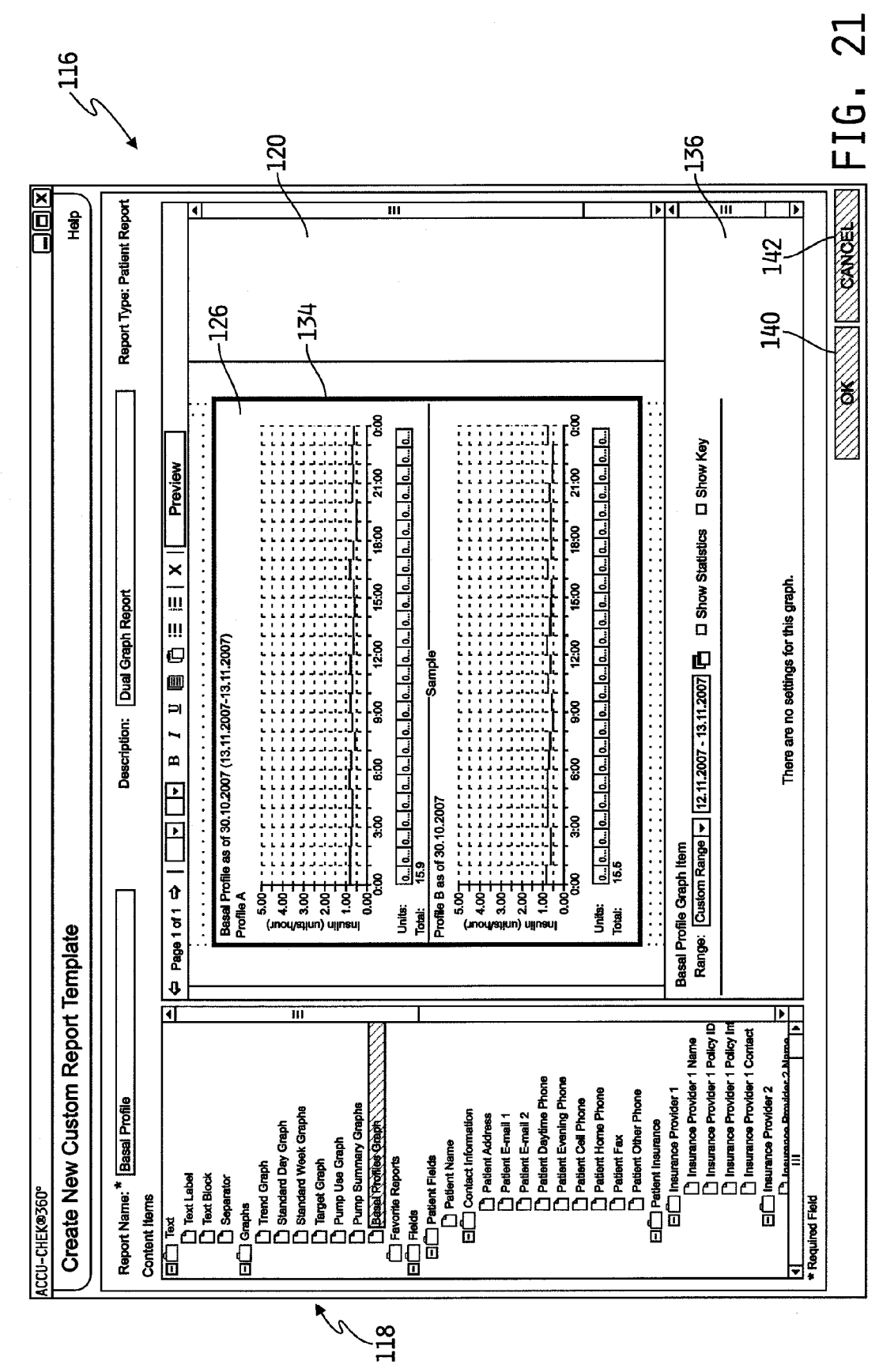

When building custom report templates, the user can adjust the scale and content of the graphs and other information that have been dragged and dropped to template section 120 in the same manner as described above. For example, if the user desires to alter the graph 126, he or she can position a cursor over the graph and click. This causes a boundary box 134 to be displayed around graph 126 and a graph content menu 136 to be displayed at the bottom of template section 120 (FIG. 20). The cursor can then be used to expand or contract boundary box 134 to increase or decrease the size of graph 126. Changing the size of graph 126 also causes the x and y axes to be relabeled as needed. Note that in FIG. 20, graph 126 included slide bar 138 because graph 126 is not large enough to appropriately display the entire graph. When graph 126 is sufficiently enlarged, slide bar 138 disappears (FIG. 21). Graph content menu 136 allows the user to display the graph key, statistics and to otherwise alter the content and form of graph 126 in the same manner as described in connection with creating custom letter templates.

Figure 22:
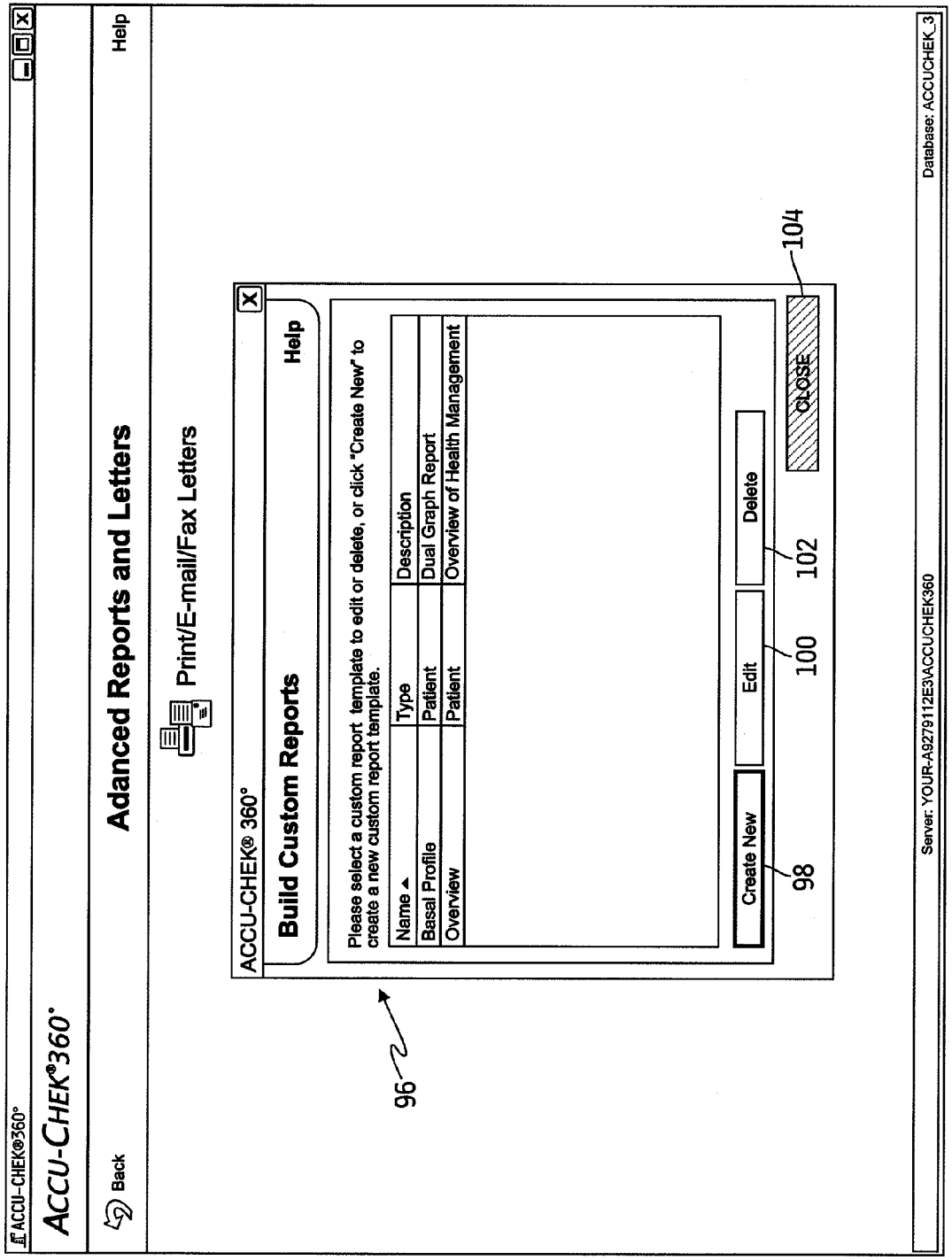

When the user is satisfied with the content of template section 120, he or she selects "OK" icon 140 to save the template. Selecting "OK" icon 140 returns the user to "reports menu" 96 which now includes a newly created Basal Profile report (FIG. 22). Alternatively, the user can select "cancel" icon 142 to abandon the operation and return to "reports menu" 96. Report templates can be deleted and edited in the same manner as described above by selecting icons 100 or 102. Selecting the "close" icon 104 returns the user to the "advanced reports and letters" menu 14.

Figure 23:
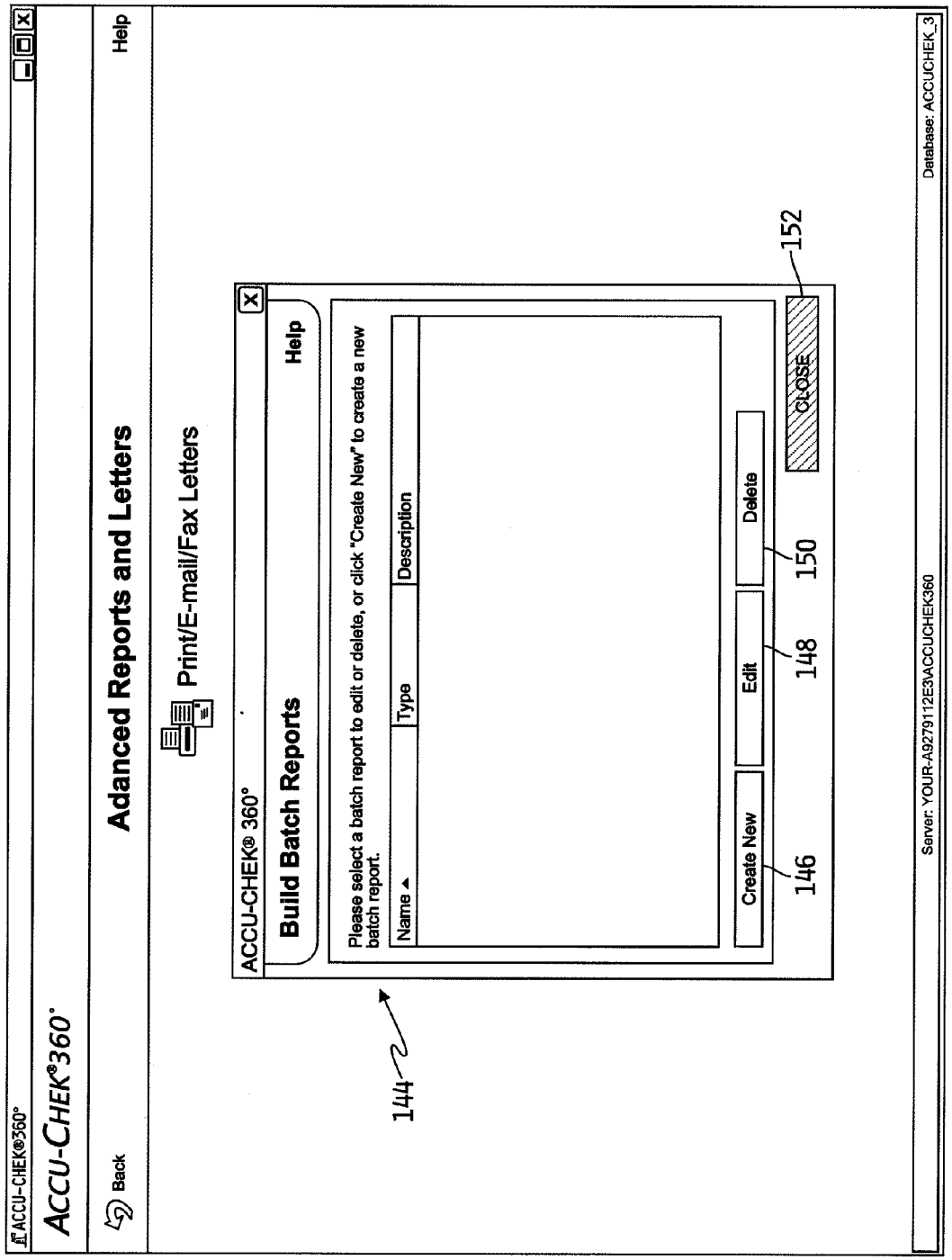

Referring again to FIG. 2, selecting "build batch reports" icon 24 displays a "batch reports menu" 144 that lists the available batch reports stored in the system (FIG. 23). A batch report is a combination of previously defined report templates that are stored in the system. In the example shown in FIG. 23, no batch reports have been defined. "Batch reports menu" 144 includes a "create new" icon 146, an "edit" icon 148, a "delete" icon 150 and a "close" icon 152.

Figure 24:
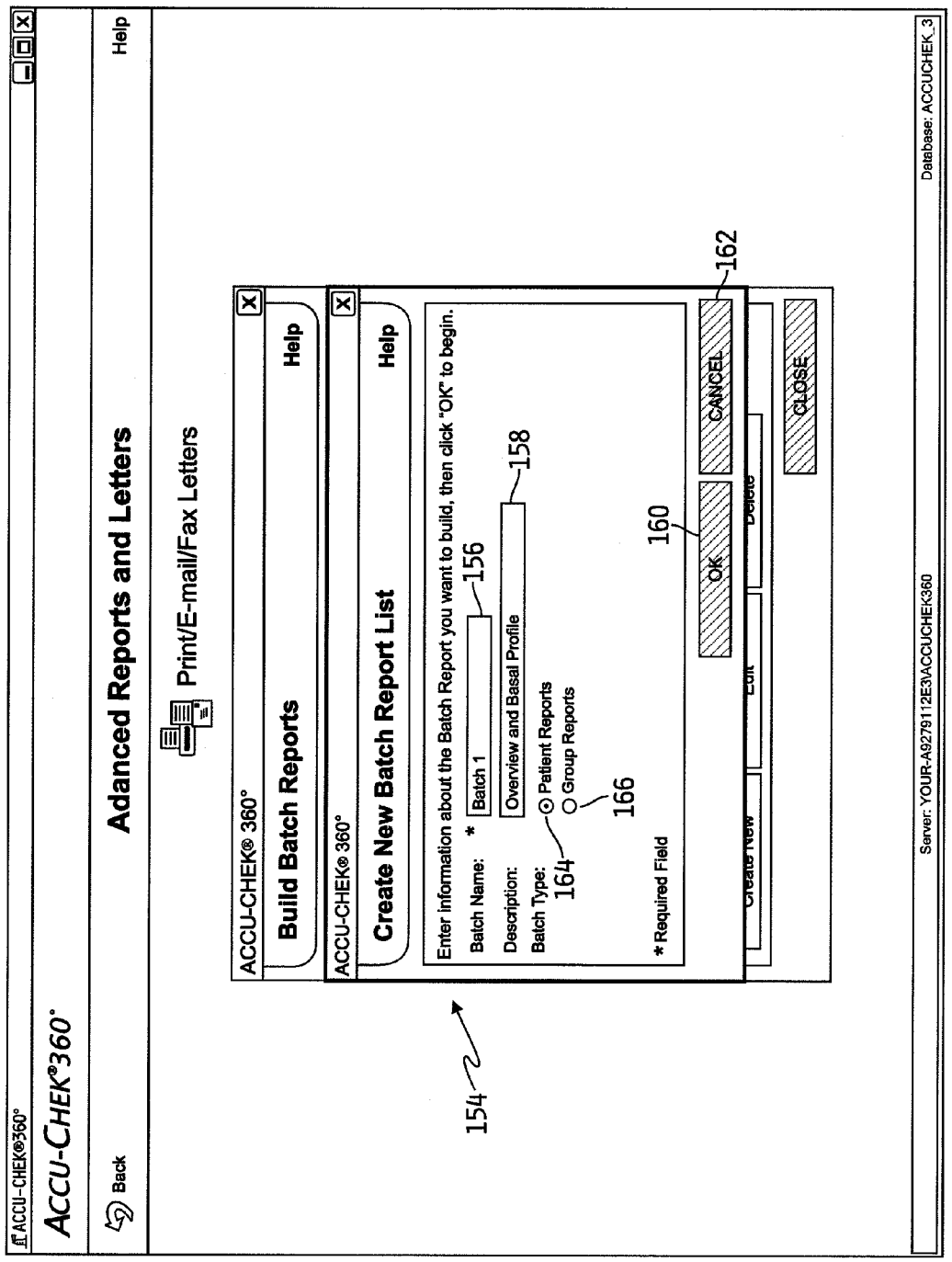

To create new batch report templates, the user selects "create new" icon 146 which causes "create new batch report" screen 154 to display (FIG. 24). "Create new batch report" screen 154 includes a text box 156 for entering the name of the new batch report and a text box 158 for entering a description of the new report. Entering text in boxes 156 and 158 causes "OK" icon 160 to become active. "Create new batch report" screen 154 further includes a "cancel" icon 162. As with the "create new report" screen 106, screen 154 allows the user to select a "patient report" option 164 or a group report option 166.

Figure 25:
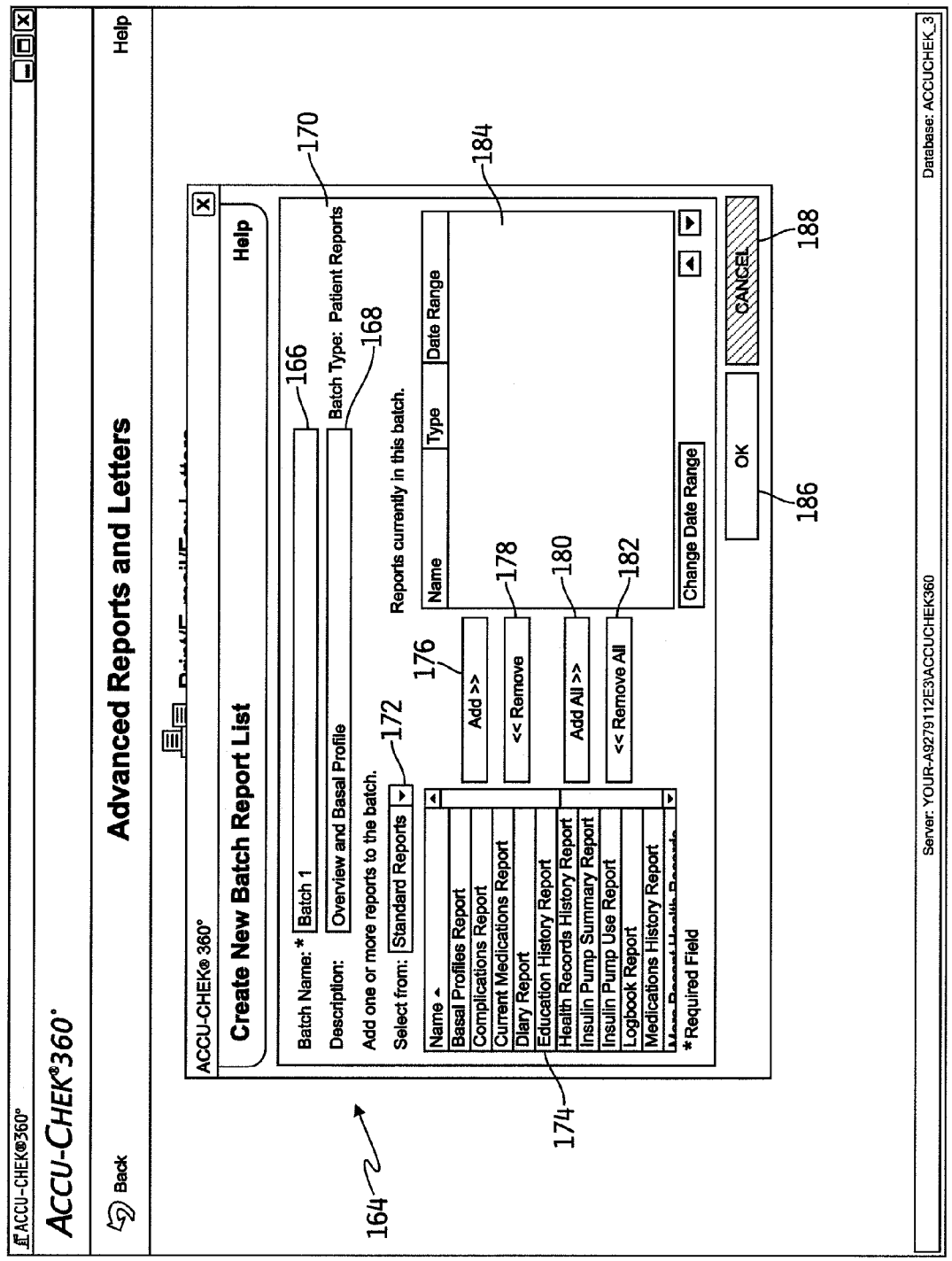
Figure 26:
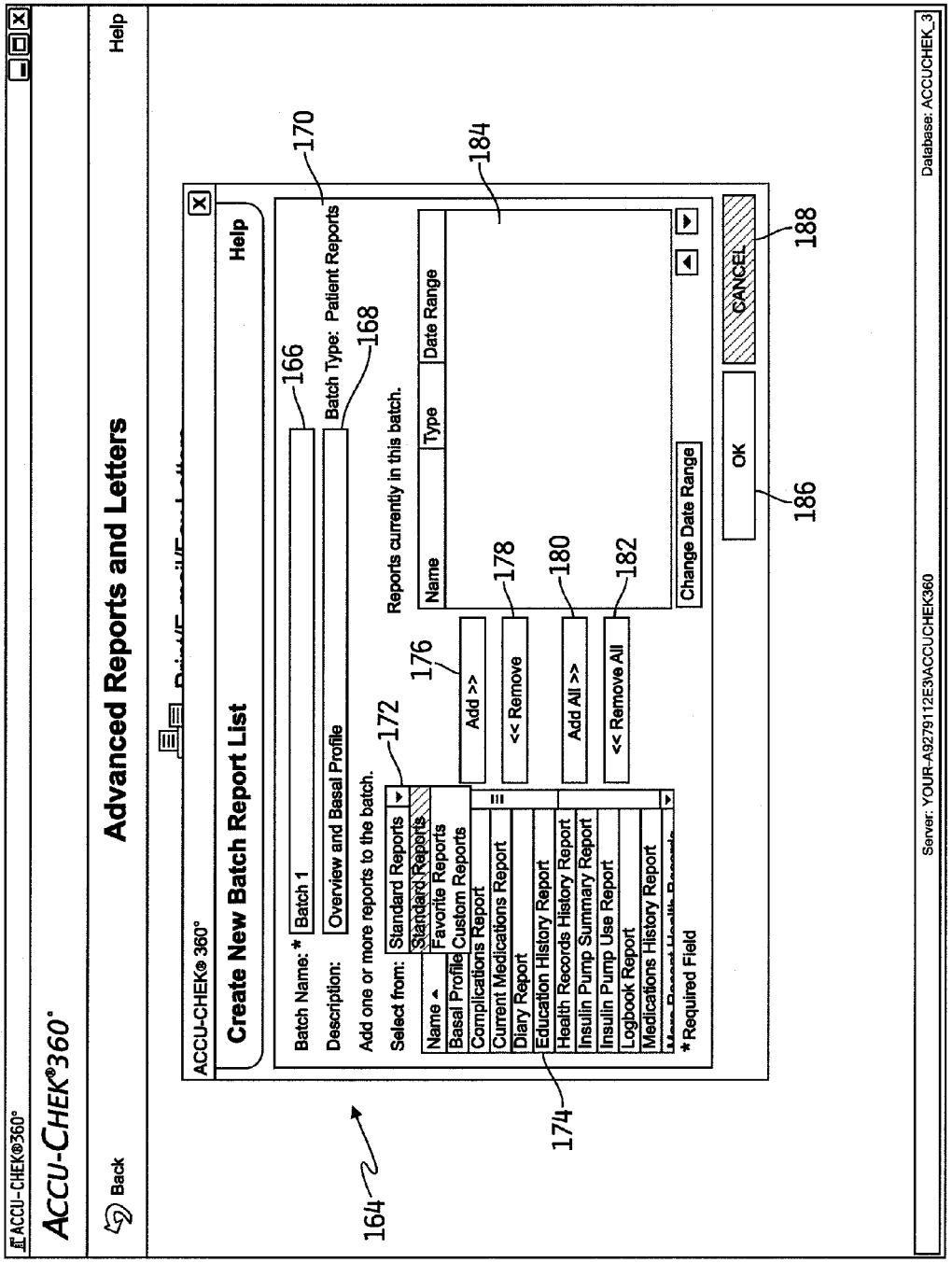
Figure 27:
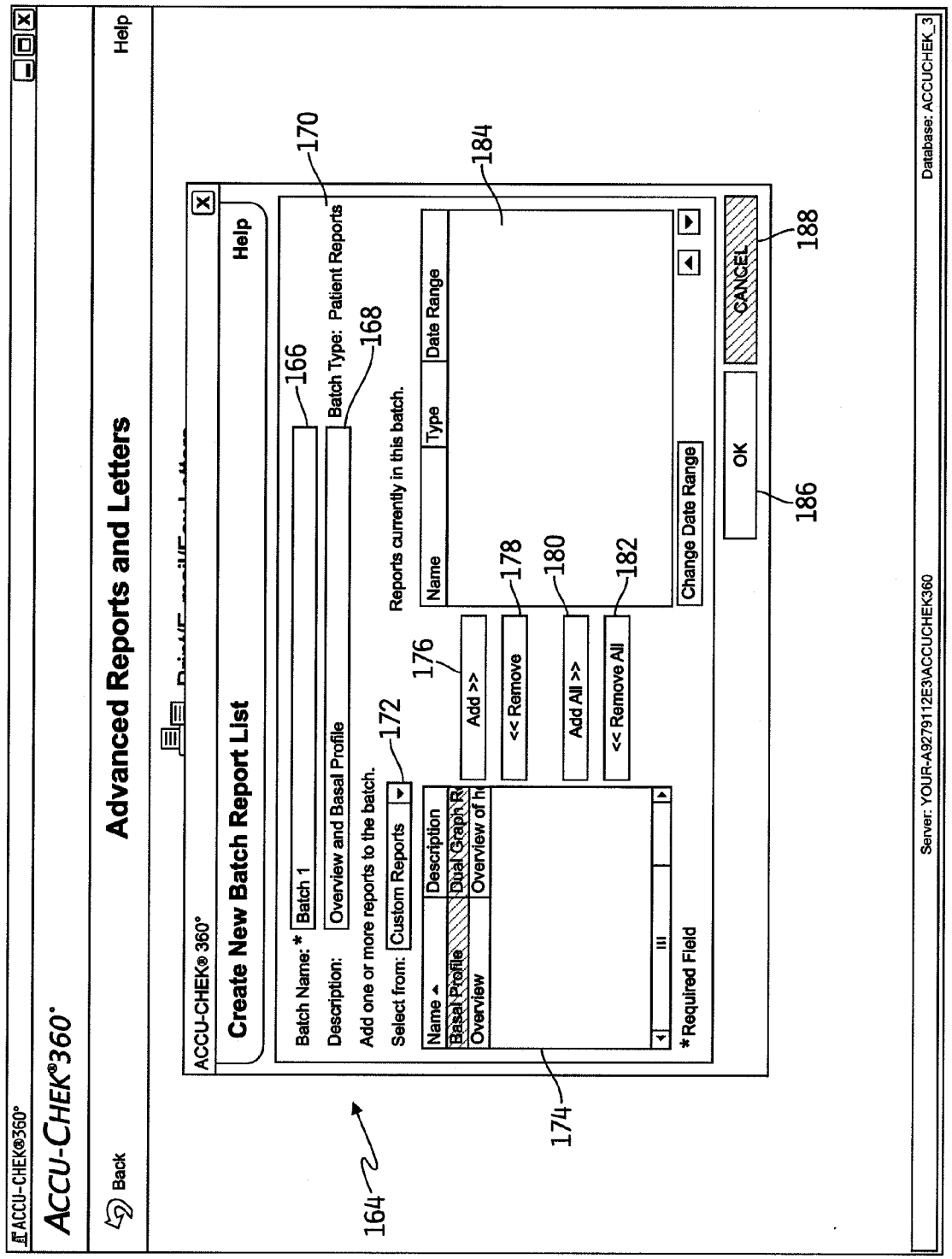
Figure 28:
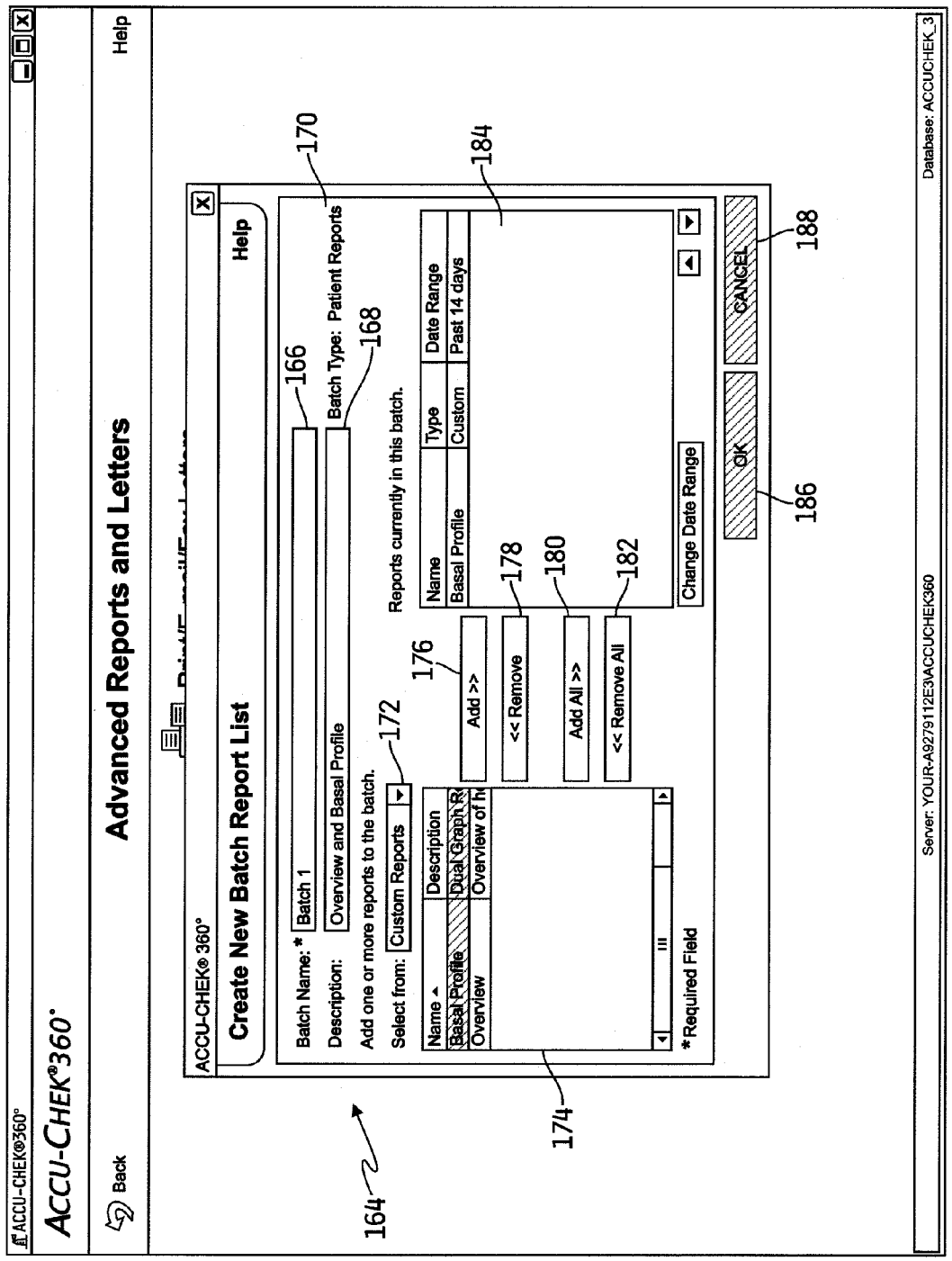

After entering the batch report name and description, selecting "OK" icon 160 displays a "create new batch report" list 164 (FIG. 25). List 164 displays the report's name in field 166 and the description in field 168. List 164 also identifies the report type in field 170. List 164 further includes a drop down menu 172 that allows the user to select between various report categories, such as standard reports, favorite reports and custom reports (FIGS. 25 and 26). For example, in FIG. 25, the standard reports category is selected in menu 172 and a list of standard reports stored in the system database appears in list field 174. Selecting "custom reports" from menu 172 displays the stored custom reports in field 174 (FIG. 27). "Create new batch report" list 164 further includes "add" icon 176, "remove" icon 178, "add all" icon 180 and "remove all" icon 182. List 164 further includes an included reports field 184, "OK" icon 186 and "cancel" icon 188.

Figure 29:
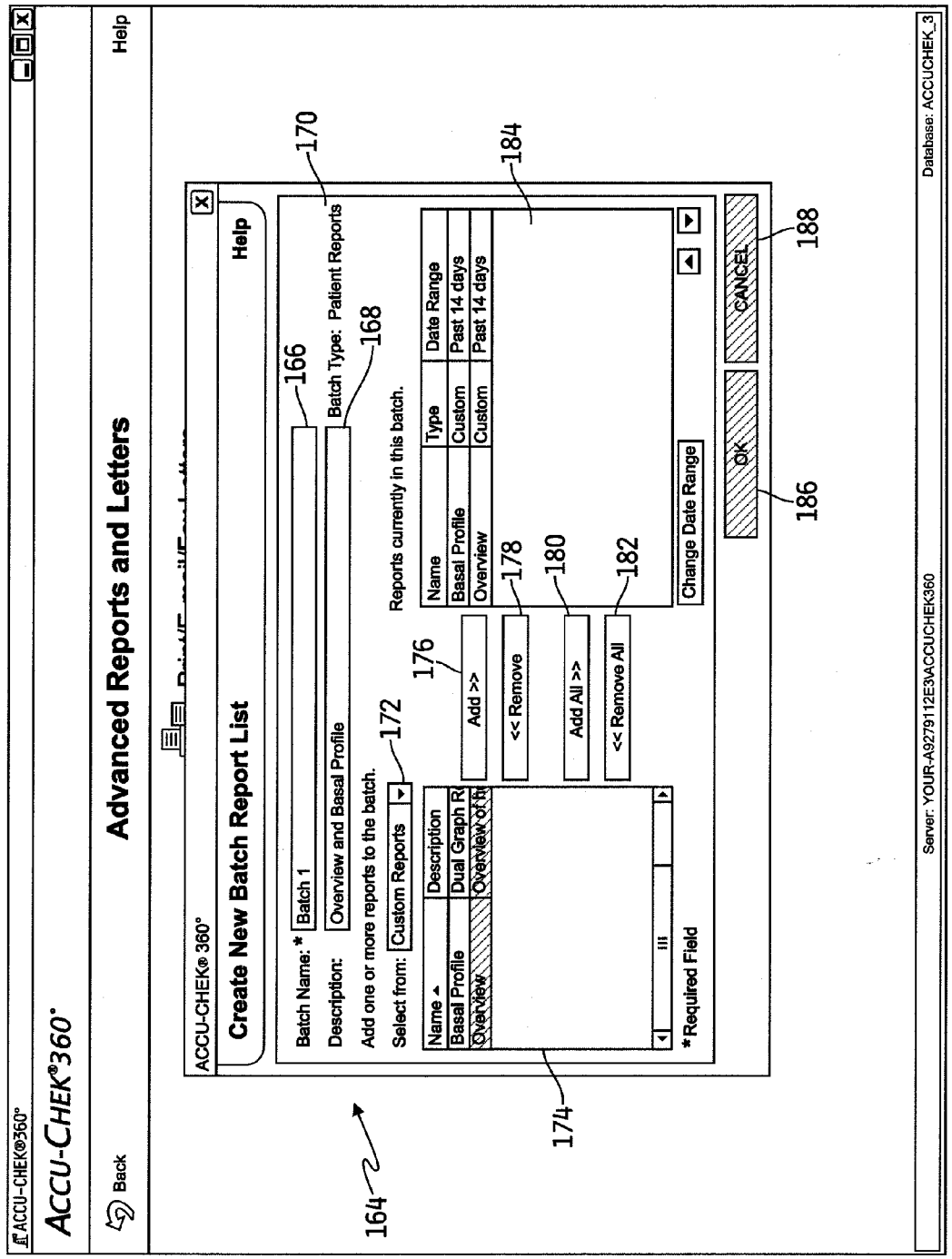

To create a batch report, the user highlights the desired report (such as the basal profile report as shown in FIG. 27) and selects "add" icon 176. This causes the desired report to be displayed in included report field 84. Highlighting the "overview" report and selecting "add" icon 176 causes that report to be added to included reports field 184 as well (FIG. 29). To remove a report from included report field 184, the user highlights the report and selects "remove" icon 178. Selecting "add all" icon 180 or "remove all" icon 182 will display all of the reports shown in field 174 in included report field 184 or remove all of the reports shown in included report field 184, respectively.

Figure 30:
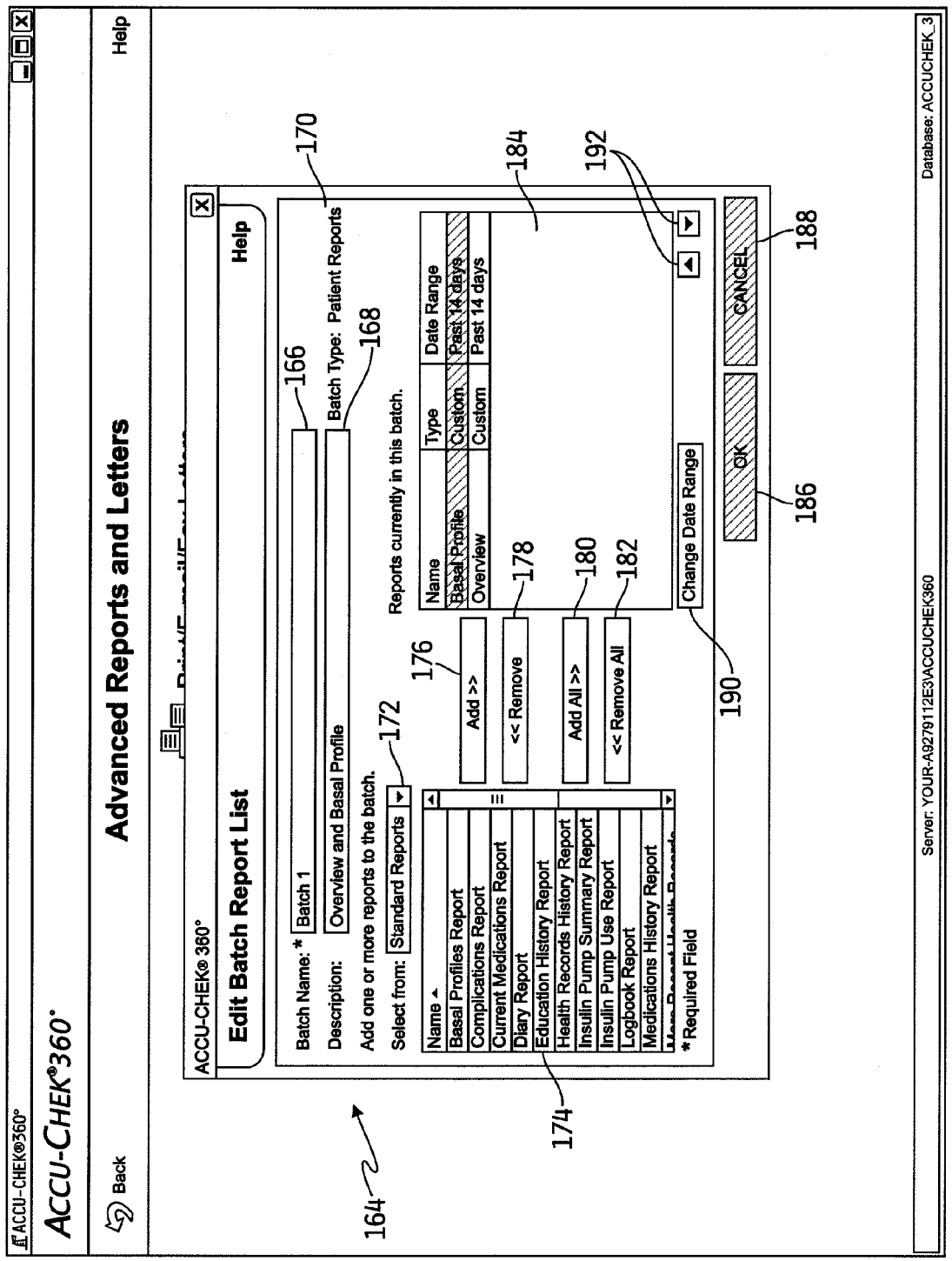
Figure 31:
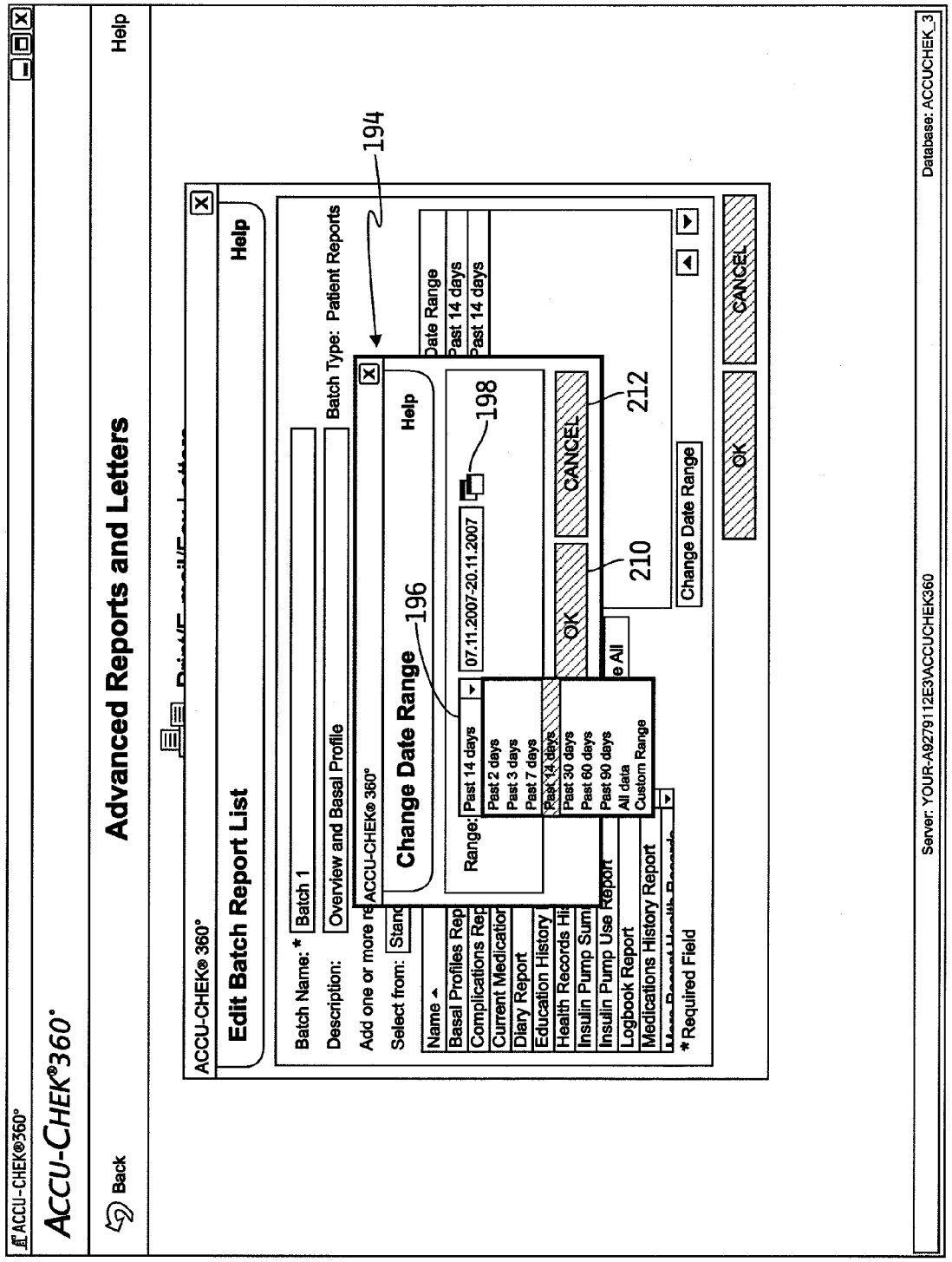
Figure 32:
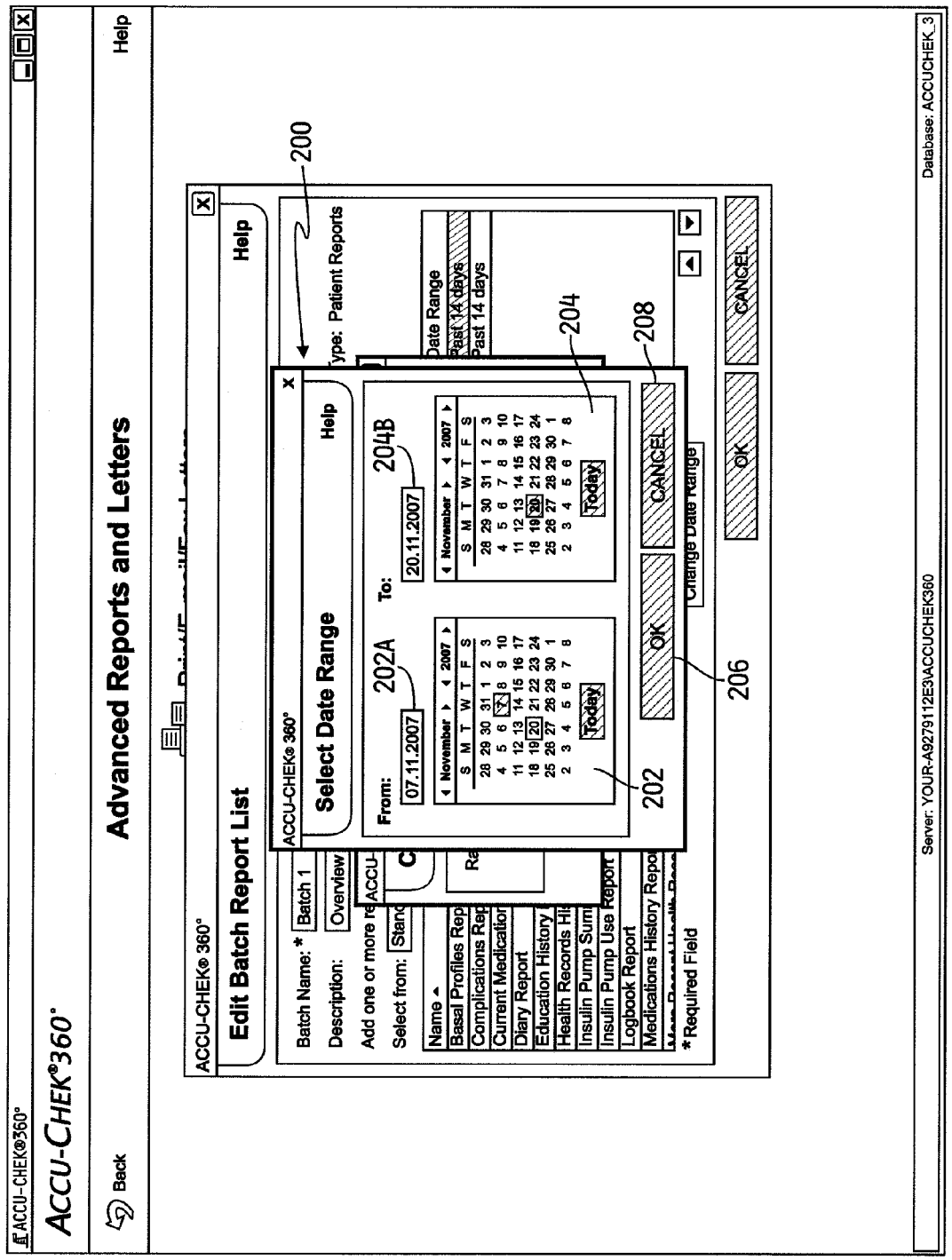

Once a report has been added to included reports field 184, the user may change the report date range. This is done by highlighting a report in field 184, which activates "change date range" icon 190 and scroll arrows 192 (FIG. 30). Selecting "change date range" icon 190 displays a "change date range" screen 194 (FIG. 31). The user can then select the desired date range from drop down menu 196. Alternatively, the user may select "calendar" icon 198 to display a select date range screen 200 (FIG. 32). The user can then select the desired dates from calendars 198, 200 as known in the art or enter the desired dates in text boxes 202A, 204B. When the user has selected the desired date range, selecting "OK" icon 206 returns the user to "change date range" screen 194. Alternatively, the user can abandon the operation by selecting "cancel" icon 208. Similarly, selecting "OK" icon 210 or "cancel" icon 212 from "change date range" screen 194 either saves the changes or abandons the operation.

Figure 33:
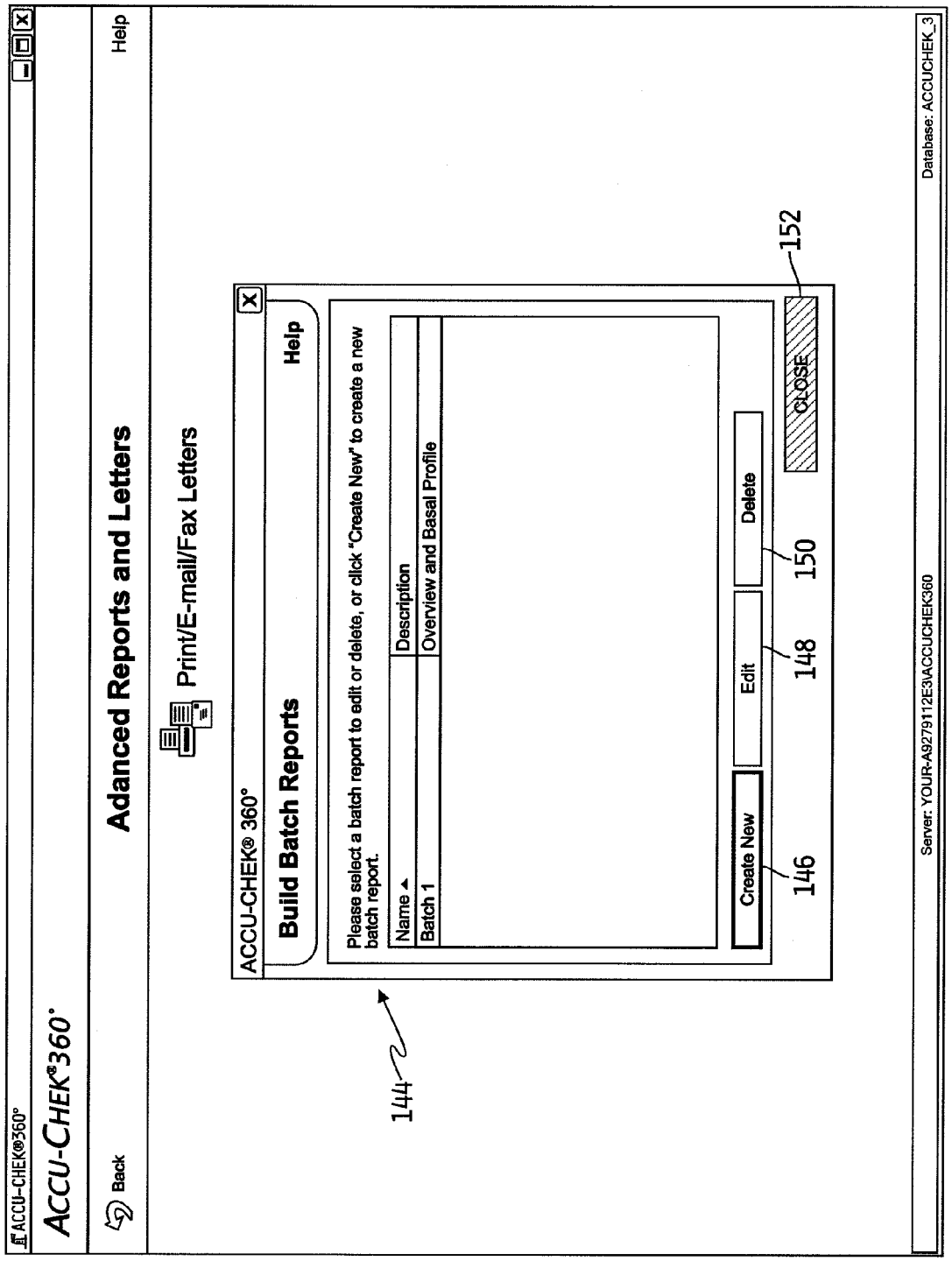

When the user is satisfied with the reports to be included in the new batch report, he or she selects "OK" icon 186 which returns the user to "build batch reports" screen 144, which now displays the newly created batch report (FIG. 33). Alternatively, selecting "cancel" icon 188 will abandon the operation and return the user to "build batch report" screen 144. To edit a batch report, the user highlights the report on screen 144 and selects the "edit" icon 148. This returns the user to an "edit batch report" screen (not shown) similar to list 164 and allows the user to edit the report through the use of icons 176 through 182. To delete a batch report, the user highlights the report on screen 144 and selects "delete" icon 150.

Note that in one embodiment of the invention, batch reports can be created that include other batch reports. To do so, the user simply selects the "create new" icon 146 to be taken to the "create new batch report" screen 154. The use then enters the name and description of the report as described above. List 164 will then be displayed. Previously stored batch reports will be included in field 174 when the appropriate report category is selected from menu 172. The batch reports could be stored in a separate category, such as one entitled "batch reports," or could be stored as custom or favorite reports. The previously defined batch reports are then added to "included reports" field 184 as described above and other batch reports or individual reports are added to the field to create a new batch report.

Figure 34:
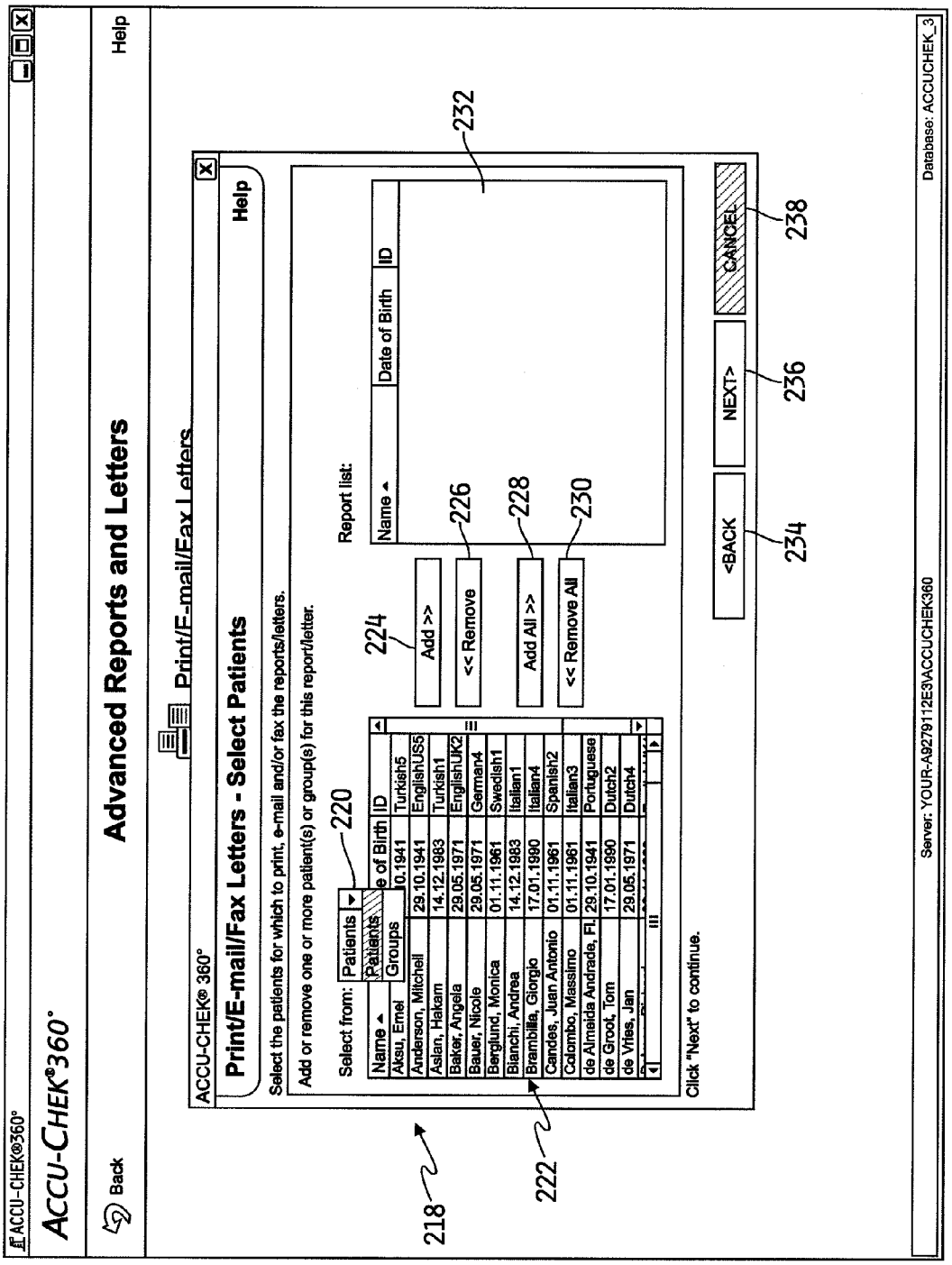
Figure 35:
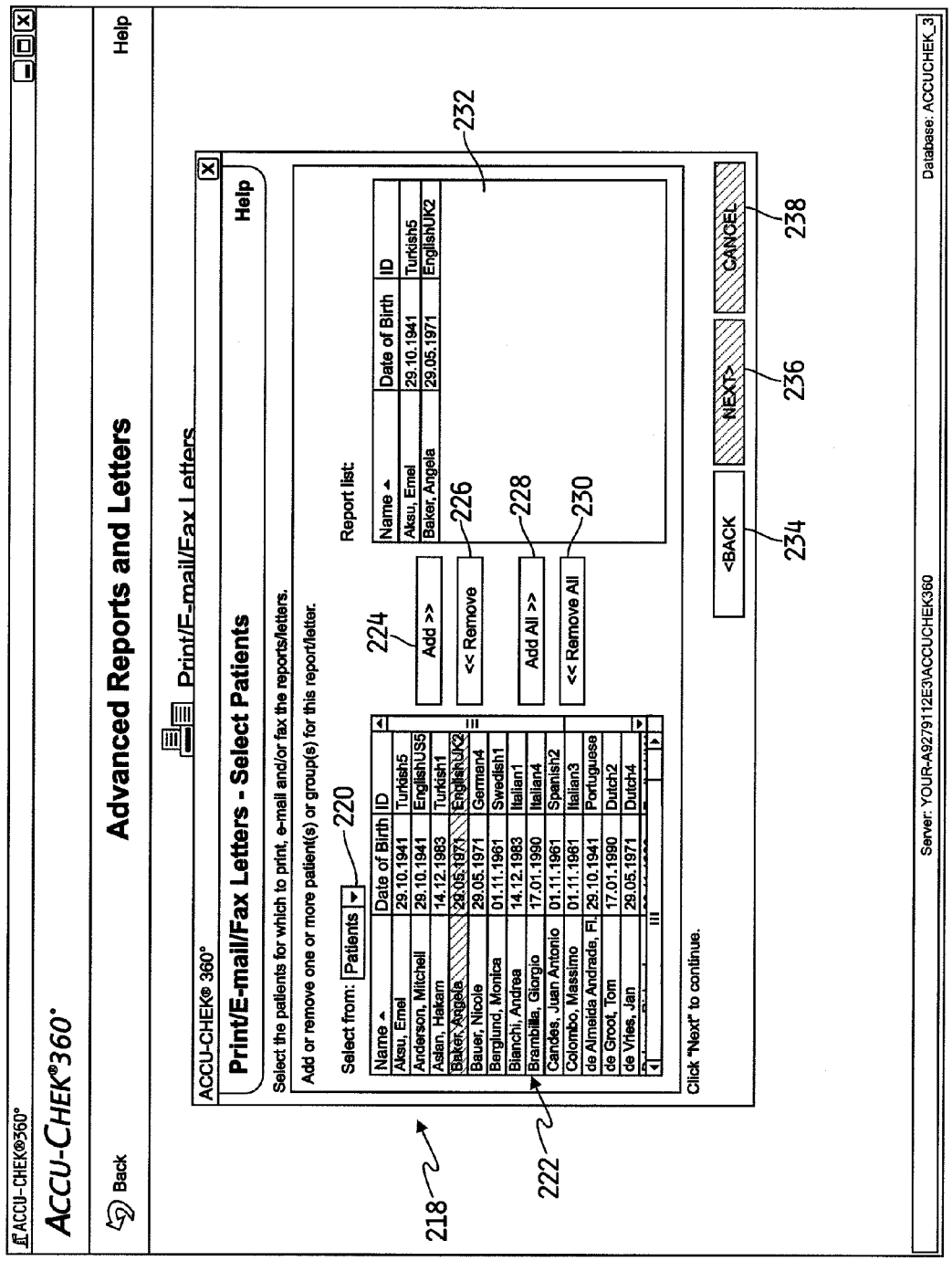

Return again to FIG. 2, selecting "print/e-mail/fax letters" icon 16 displays a "select patients" screen 218 (FIG. 34). "Select patients" screen 218 includes a drop down menu 220 that allows the user to display either a list of individual patients or a list of patient groups in field 222. "Select patients" screen 218 further includes "add" icon 224, "remove" icon 226, "add all" icon 228 and "remove all" icon 230. Screen 218 further includes an included patient field 232, a "back" icon 234, a "next" icon 236 and a "cancel" icon 238. To add a patient or group to included patient field 232, the user highlights the desired patient name and selects "add" icon 224 (FIG. 35). This causes the patient's name to be displayed in included patient field 232. As shown in FIG. 35, two patients have been selected. If the "groups" option had been selected from drop down menu 220, the selected patient groups would be included in field 232.

Figure 36:
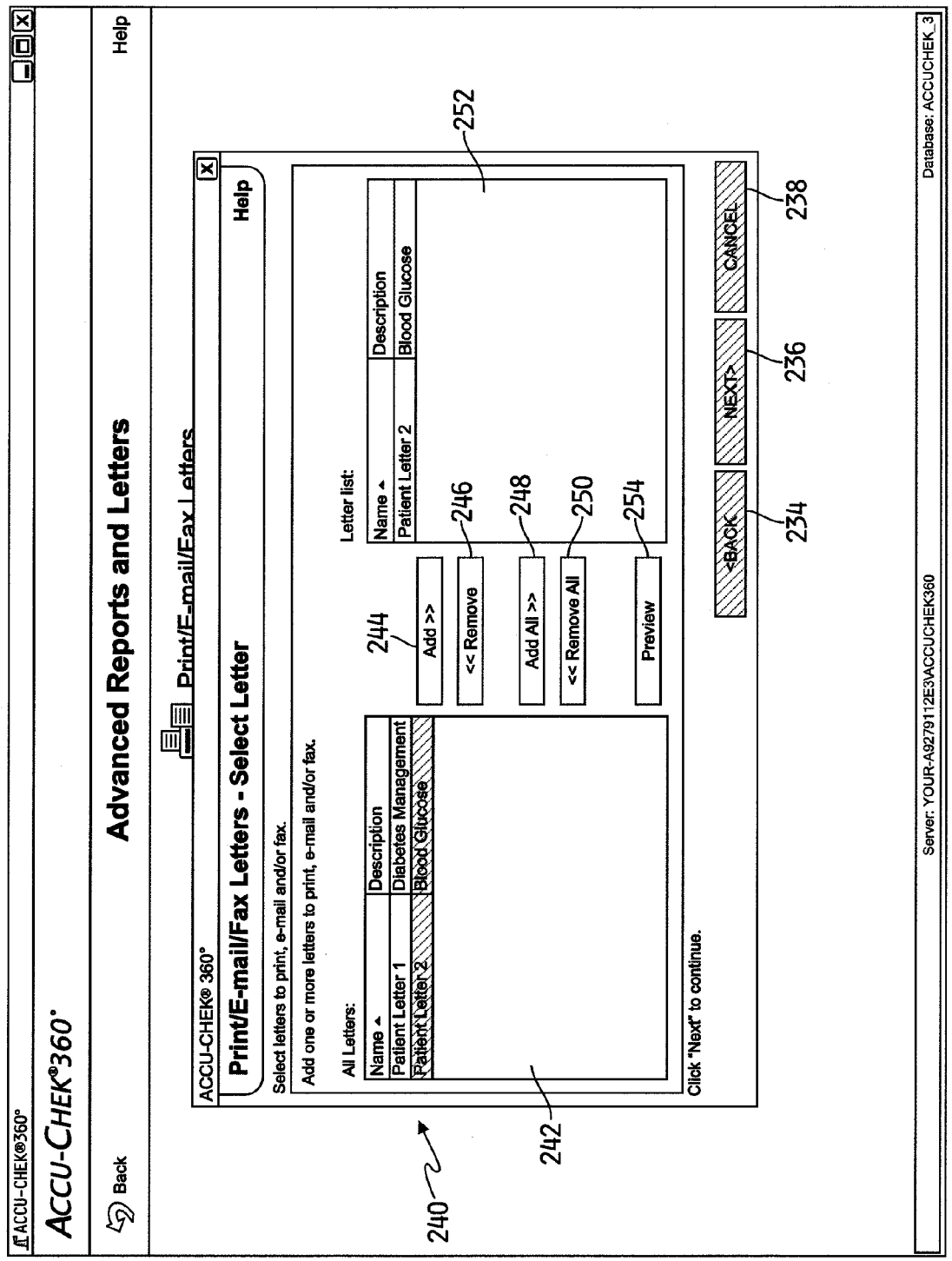

Once the user has populated field 232 as desired, he or she selects "next" icon 236 to display "select letter" screen 240 (FIG. 36). Screen 240 includes a listing of the available letters in field 242, "add" icon 244, "remove" icon 246, "add all" icon 248 and "remove all" icon 250. Screen 240 further includes an included letters field 252. To add a letter to field 252, the user highlights the letter in field 242 and selects "add" icon 244. Icons 246-250 are utilized to remove added letters from field 252 or to add and remove all letters to or from field 252 in the same manner as described above. Icons 234 and 236 are used to navigate between the various screens. Note that "select letter" screen 240 further includes a "preview" icon 254 that allows the user to preview the letter to be generated in a manner similar to that described above.

Figure 37:
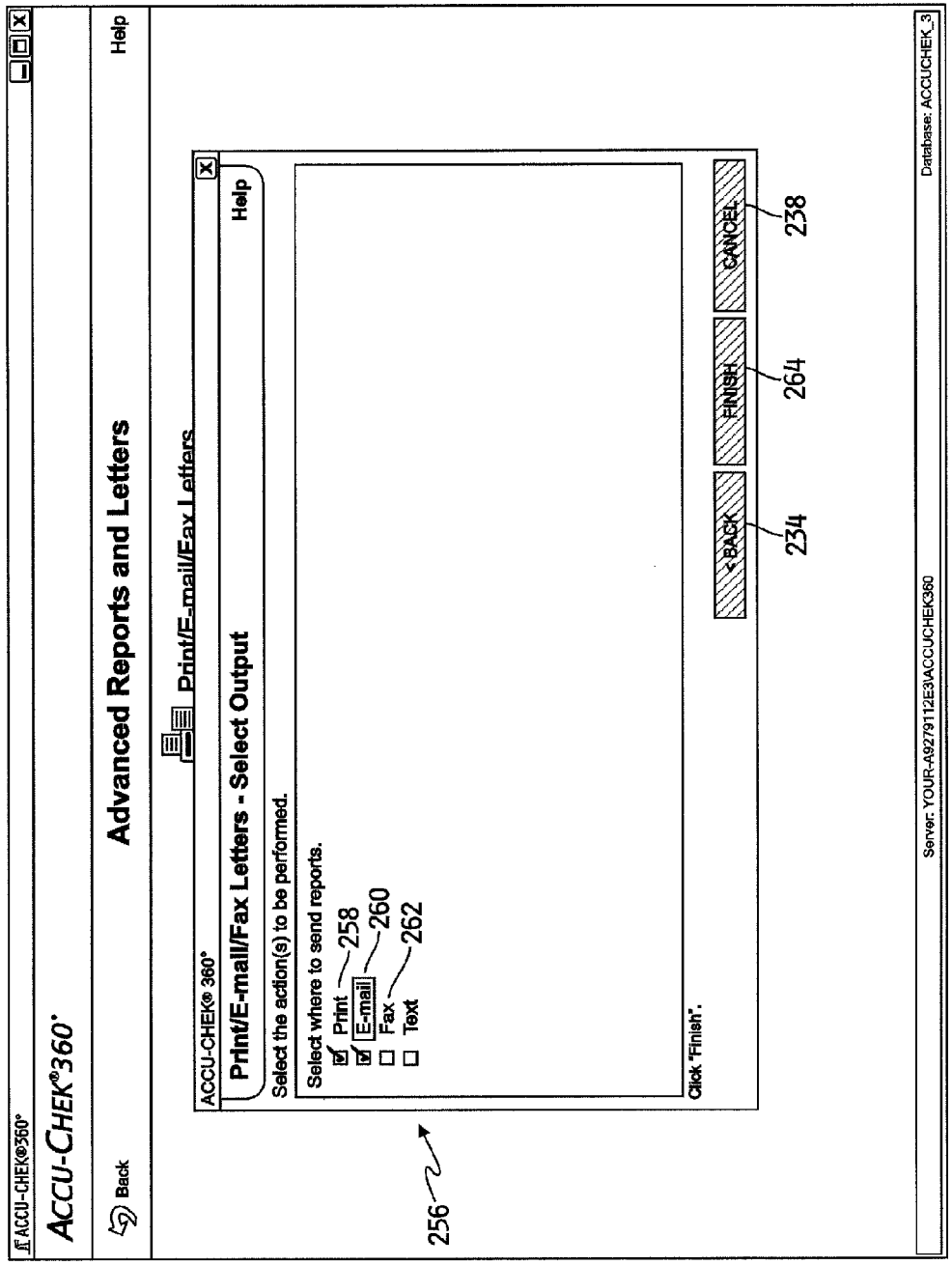

After the user has populated field 252, he or she selects "next" icon 236 to display "select output" screen 256 (FIG. 37). "Select output" screen 256 includes a print option 258, an e-mail option 260 and a fax option 262. Note that options for printing, e-mailing and faxing are shown only as examples. Other embodiments of the invention could utilize additional or other output devices, such as text messaging sent to a cellular phone, output to a web page or other means of communication. Note also that in other embodiments of the invention, the user can be provided with a language selection screen or drop down menu (not shown) at a desired time during the process to allow the user to select the output language for the letters. In this manner, a user who speaks one language, such as English, can generate letters to a patient who speaks another language, such as Spanish. Different languages can be selected for different patients or patient groups.

Figure 38:
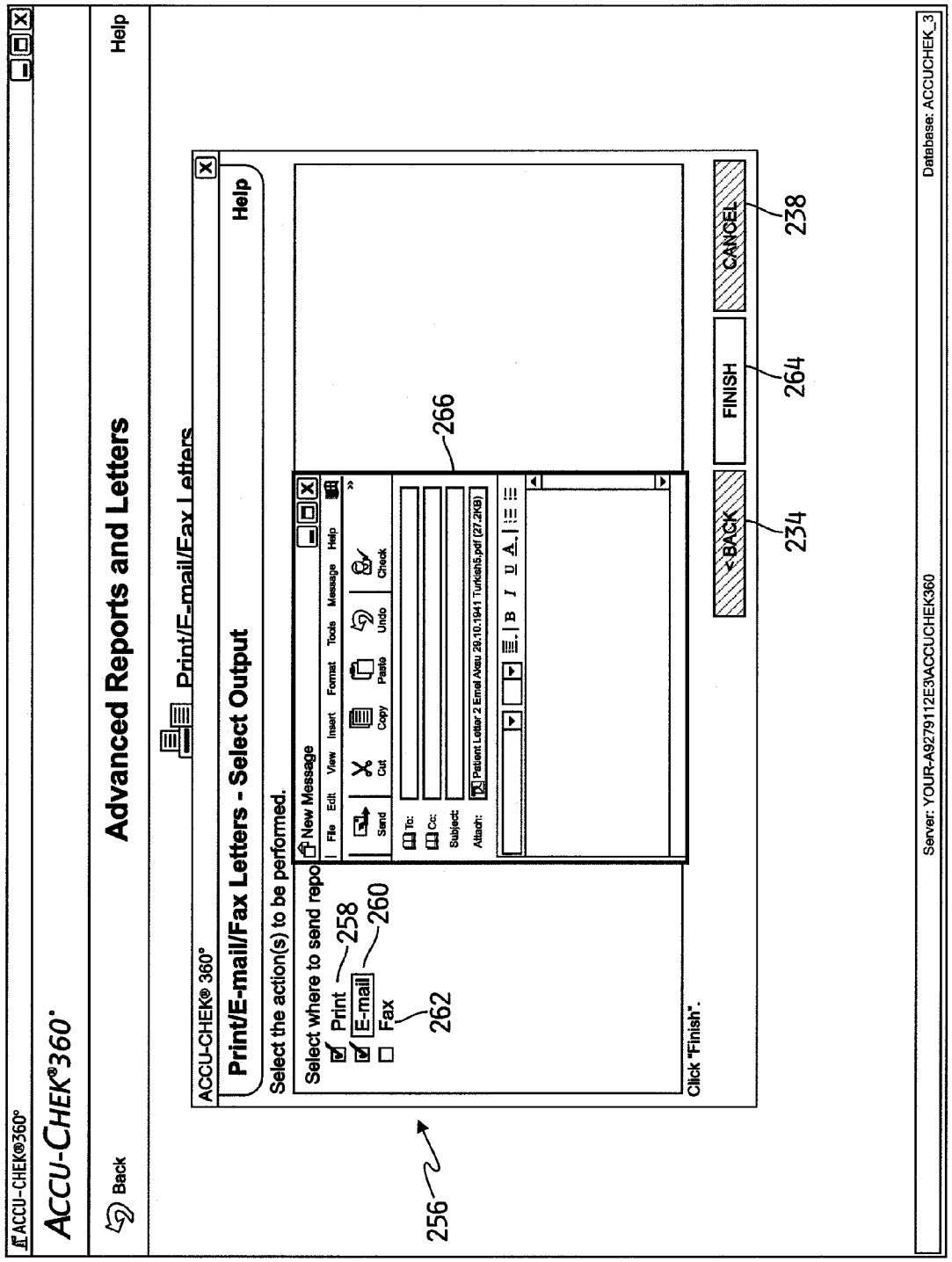

In the example shown in FIG. 37, print option 258 and e-mail option 260 have been selected. Once the desired options are selected, selecting "finish" icon 264 begins the letter output process. For example, selecting icon 264 will cause the system to retrieve from the database the information required to complete the selected letter templates for each patient or group. For example, the system will retrieve patient names, blood glucose readings or other information defined by the template. The selected letters for the selected patients will then print to a previously selected default printer. Alternatively, the system could be configured to display a printer menu so that a different printer could be selected. Similarly, selecting "finish" icon 264 will display a blank e-mail message 266 with the previously selected patient letter or letters attached (FIG. 38). The user can then input the recipient's address and a message before sending the e-mail. In the example shown in FIG. 37, had fax option 262 also been selected, selecting "finish" icon 264 would activate the fax drivers to transmit the selected letters.

Note that selecting "finish" icon 264 causes the system to output the letters in all of the selected output formats but that the sequence in which this occurs is not relevant. For example, e-mail message 266 shown in FIG. 38 could be displayed prior to the various print options discussed above.

Figure 39:
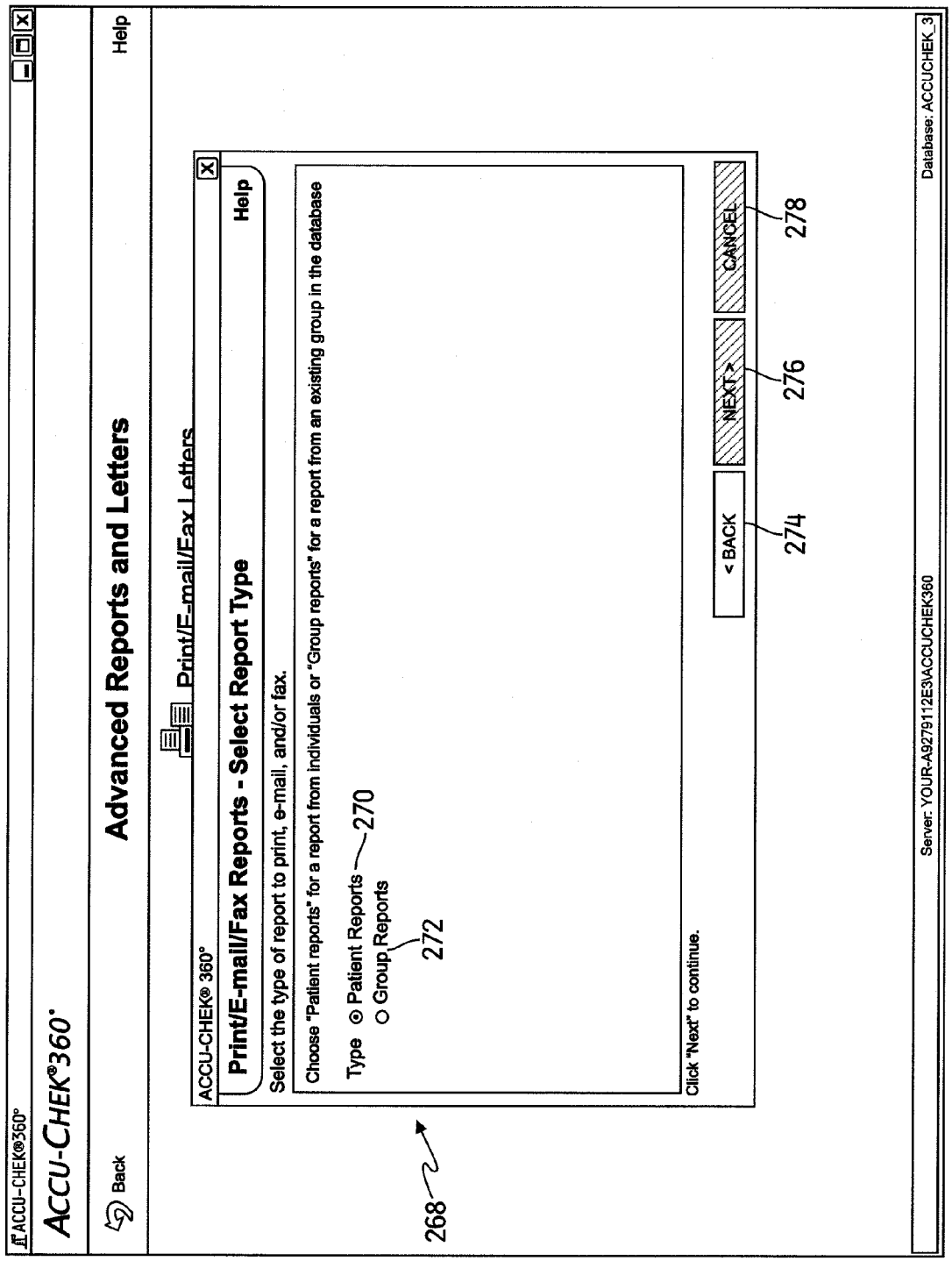
Figure 40:
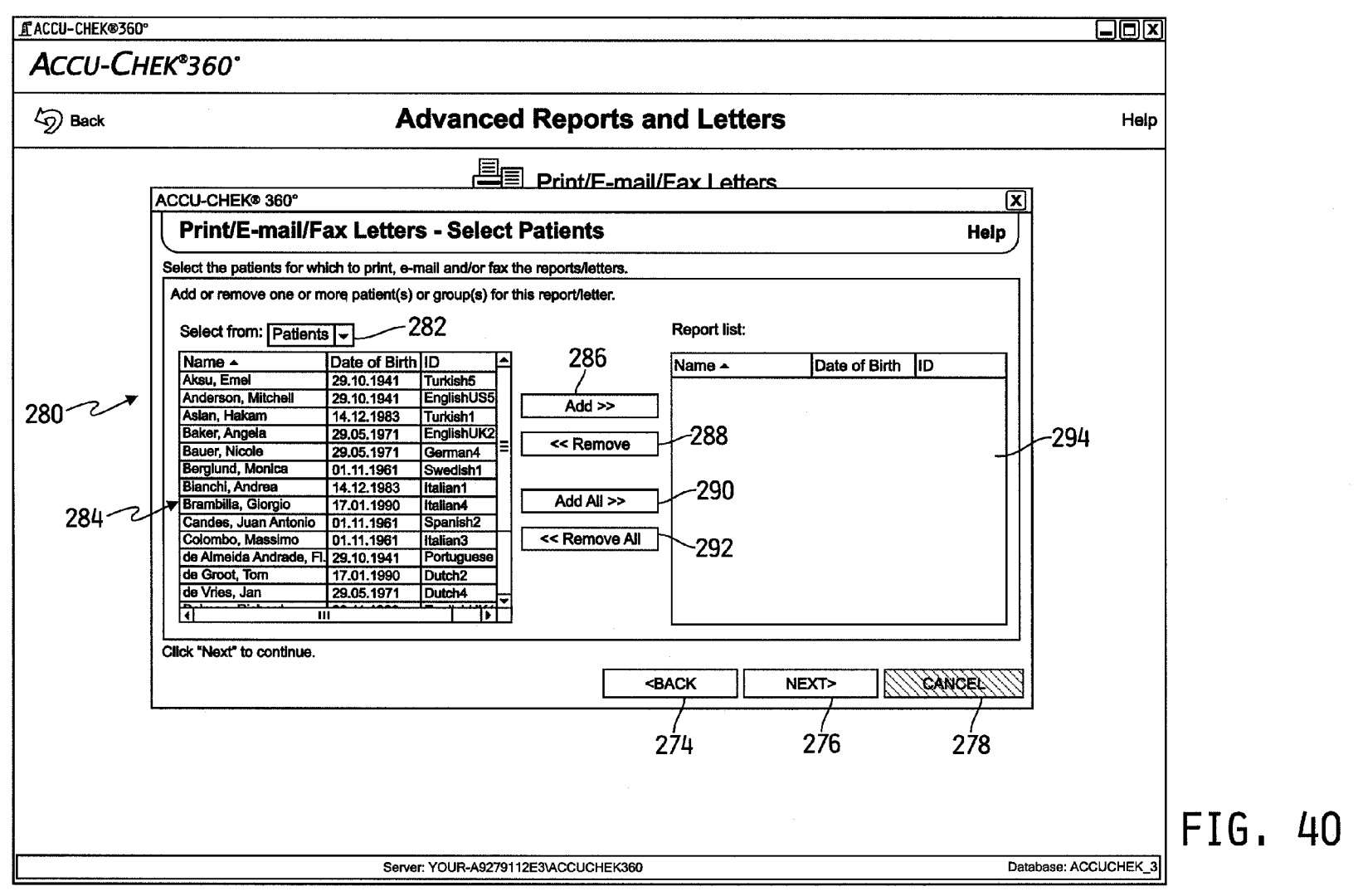
Figure 41:
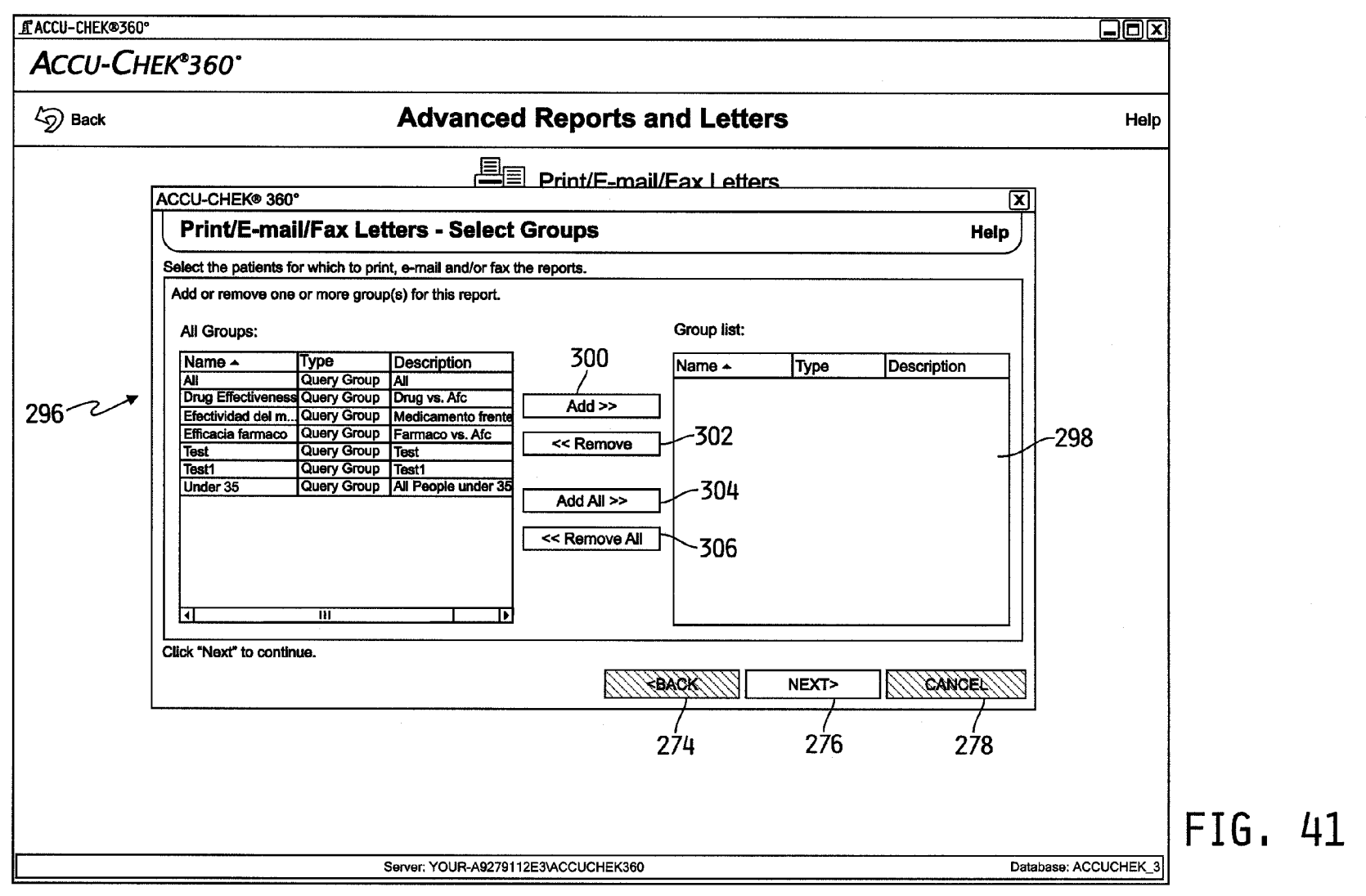
Figure 42:
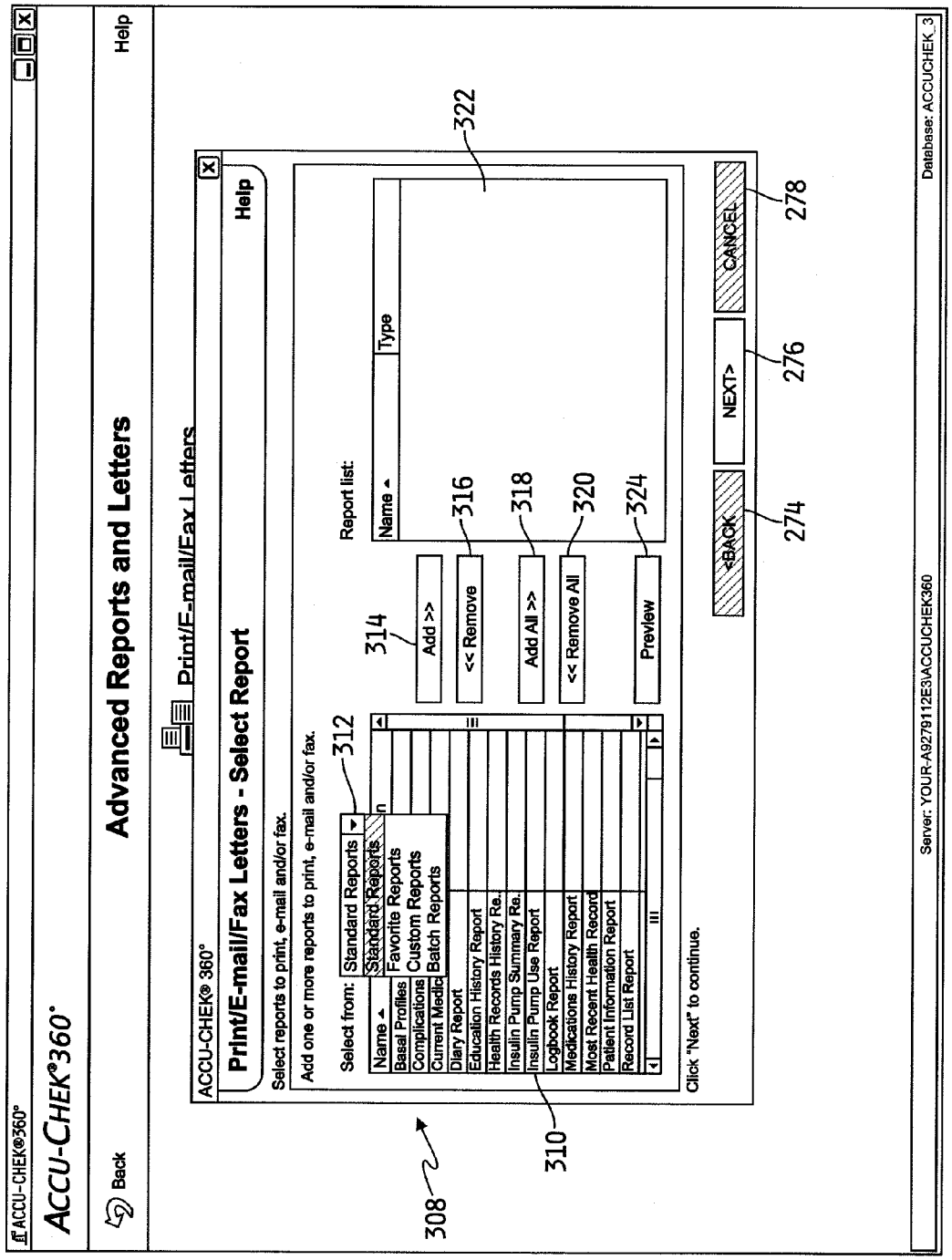

Returning again to FIG. 2, selecting "print/e-mail/fax" icon 18 displays a "select report type" screen 268 (FIG. 39). Screen 268 allows the user to select a patient report option 270 or a group report option 272. Selecting patient report option 270 and "next" icon 276 displays a "select patients" screen 280 as shown in FIG. 40. Note that although patient report option 270 was selected, drop down menu 282 also includes a "group reports" category (not shown) which would cause a listing of the patient groups to be displayed in field 284 as opposed to the patient listing as shown in FIG. 40. Icons 286, 288, 290 and 292 are used to add and remove patients from field 294 in the same manner as described above. Note also that selecting group reports option 272 in FIG. 39 displays "select groups" screen 296 that allows the user to populate included group field 298 using icons 300, 302, 304 and 306 (FIG. 41).

After the desired patients or groups have been selected, selecting "next" icon 276 displays a "select reports" screen 308. "Select reports" screen 308 includes a report list field 310, the contents of which are dictated by the options selected from drop down menu 312. Icons 314, 316, 318 and 320 are used to populate included report field 322 in the same manner as previously discussed. Screen 308 also includes a "preview" icon 324 for previewing the selected reports. Once field 322 has been populated, selecting "next" icon 276 causes a select output screen identical to that shown in FIG. 37 to be displayed, except that the screen bears the heading "print/e-mail/fax reports—select output." The reports are then outputted in the same manner as described above in conjunction with the letters output.

While this invention has been described as having an exemplary design, the present invention may be further modified within the spirit and scope of this disclosure. For example, the system software can be run on any processing device with sufficient memory and other system requirements, such as a cellular phone, PDA, blood glucose meter or other device. Although the system has been described for use in connection with the treatment of diabetes, it can also be used in connection with other medical conditions. Furthermore, the various types of reports, letters, graphs and content are shown merely for purposes of illustration. Other reports, letters, graphs and content could also be used. It should further be noted that use of the term "graph" in this description is intended to cover any type of graphical display of information, such as histograms, pie charts, line graphs, bar charts, etc. Similarly, what is described as a report in the discussion above could be considered a letter and what is described as letter could be considered a report. Accordingly, these terms can be considered interchangeable and the software described above could combine the custom report building functionality with the custom letter building functionality. The same is true of the print/e-mail/fax functionalities. Thus, this application is intended to cover any variations, uses, or adaptations of the invention using its general principles. Further, this application is intended to cover such departures from the present disclosure as come within known or customary practice in the art to which this invention pertains.

What is claimed is:

1. A system for reporting information comprising:
a computing device having a memory and a processor;
a display configured to receive commands from the computing device; and
a software program including a plurality of instructions, the software program stored in the memory and interpretable by the processor of the computing device such that when interpreted by the processor the software program causes the computing device and the display to cooperate to:
display a menu screen having a first selectable option and a second selectable option,
display, upon selection of the first selectable option, a report preparation screen having a template creation selectable option and a list area,
display, upon selection of the template creation selectable option, a template creation screen having a content area and a template area, the content area comprising a plurality of content items having at least one fillable field, position, upon dragging and dropping at least one content item from the content area into the template area, the at least one content item at a location in the template area where the content item was dropped,
display, upon positioning the at least one content item in the template area, a third selectable option on the template creation screen,
generate and store in the memory, upon selection of the third selectable option, a document template comprising the at least one content item positioned within the template area,
display, upon selection of the third selectable option, the report preparation screen, the list area of the report preparation screen having a selectable document template icon for the document template stored in the memory; and
display, upon selection of the selectable document template icon, a patient information selectable option, selection of the patient information selectable option presenting an option for selecting one of a patient group and an individual patient, selection of the one of the patient group and the individual patient importing medical information relating to the one of the patient group and the individual patient into the fillable fields of the content items of the document template represented by the selectable document template icon.

2. The system of claim 1, wherein the display comprises at least one of a PDA, a printer, a fax machine, a telephone, and a monitor.

3. The system of claim 1, wherein the plurality of instructions of the software program further includes instructions that when interpreted by the processor cause the computing device and the display to cooperate to:
display, upon selection of the second selectable option of the menu screen, a patient information selectable option and a plurality of selectable document template icons, each of the selectable document template icons representing a separate document template stored in the memory, selection of the patient information selectable option presenting an option for selecting one of a patient group and an individual patient, and
import, upon selection of one of the selectable document template icons and one of the patient group and the individual patient, medical information relating to the selected one of the patient group and the individual patient into the fillable fields of the content items of the document template represented by the selected selectable document template icon.

4. The system of claim 1, wherein the plurality of instructions of the software program further includes instructions that when interpreted by the processor cause the computing device and the display to cooperate to:
display, upon selection of the selectable document template icon, a plurality of communication mode selectable options.

5. The system of claim 4, wherein the plurality of communication mode selectable options includes a plurality of options comprising options for faxing, texting, printing, and e-mailing the document template having the medical information imported into the fillable fields.

6. The system of claim 5, wherein the medical information relating to the one of the patient group and the individual patient imported into the tillable fields includes at least one of a fax number, a text receiving number, an e-mail address and an IP address, wherein selection of the communication mode selectable option for faxing causes the computing device to fax the document having the medical information imported into the tillable fields to the fax number, selection of the communication mode selectable option for texting causes the computing device to text the document template having the medical information imported into the tillable fields to the text receiving number, selection of the communication mode selectable option for printing causes the computing device to forward the document template having the medical information imported into the tillable fields to the IP address, and selection of the communication mode selectable option for e-mailing causes the computing device to send the document having the medical information imported into the tillable fields to the e-mail address.

7. The system of claim 4, wherein the plurality of content items displayed in the content area includes a plurality of items selected from the group comprising a patient contact information fillable item, a patient insurance provider information fillable item, a patient healthcare provider information fillable item, a patient demographic information fillable item, and a patient diabetes information fillable item.

8. The system of claim 4, wherein the plurality of content items displayed in the content area includes a graph template.

9. The system of claim 1, wherein the plurality of instructions of the software program further includes instructions that when interpreted by the processor cause the computing device and the display to cooperate to:
display a batch document selectable option on the menu screen, selection of the batch document selectable option causing a batch menu screen to be displayed, the batch menu screen comprising a document template area and a batch template area, the document template area comprising a plurality of selectable document template icons positionable within the batch template area.

10. The system of claim 9, wherein the selectable document template icons are includable within the batch template area by way of at least one of dragging and dropping the document template selectable indicators from the document template area to the batch template area, and selecting the selectable document template icon in the document template area then selecting an add option.

11. A system for reporting medical information in a graph comprising:
a computing device having a memory and a processor;
a display configured to receive commands from the computing device; and
a software program including a plurality of instructions, the software program stored in the memory and interpretable by the processor of the computing device such that when interpreted by the processor the software program causes the computing device to cooperate with the display to:
display a menu screen having a first selectable option and a second selectable option,
display, upon selection of the first selectable option, a report preparation screen having a template creation selectable option and a list area,
display, upon selection of the template creation selectable option, a template creation screen having a content area and a template area, the content area comprising a graph icon,
position, upon dragging and dropping the graph icon from the content area into the template area, a graph template box at a location in the template area where the graph icon was dropped,
display, upon positioning the graph icon within the template area, a third selectable option on the template creation screen,
generate and store in the memory, upon selection of the third selectable option, a document template comprising the graph template box positioned within the template area, and
display, upon selection of the third selectable option, the report preparation screen, the list area of the report preparation screen having a selectable document template icon for the document template stored in the memory;
display, upon selection of the selectable document template icon, a patient information selectable option, selection of the patient information selectable option presenting an option for selecting one of a patient group and an individual patient, selection of the one of the patient group and the individual patient importing medical information relating to the one of the patient group and the individual patient into the fillable fields of the content items of the document template represented by the selectable document template icon.

12. The system of claim 11, wherein the plurality of instructions of the software program further includes instructions that when interpreted by the processor cause the computing device and the display to cooperate to:
display, upon selection of the selectable document template icon presented in the list area, a plurality of communication mode selectable options.

13. The system of claim 12, wherein the content area further comprises a plurality of content items having at least one fillable field and being positionable, upon dragging and dropping at least one content item, within the template area of the template creation screen, selection of one of the patient group and the individual patient populating the at least one fillable field of the content items of the document template with medical information relating to the selected one of the patient group and the individual patient.

14. The system of claim 13, wherein the plurality of communication mode selectable options includes a plurality of options comprising options for faxing, texting, printing, and e-mailing the document template having the graph template box populated with medical information relating to the selected one of the patient group and the individual patient.

15. The system of claim 14, wherein the medical information relating to the selected one of the patient group and the individual patient imported into the fillable fields includes at least one of a fax number, a text receiving number, an e-mail address, and an IP address, wherein selection of the communication mode selectable option for faxing causes the computing device to fax the document template having the medical information populated in graph template box to the fax number, selection of the communication mode selectable option for texting causes the computing device to text the document template having the medical information populated in graph template box to the text receiving number, selection of the communication mode selectable option for printing causes the computing device to forward the document template having the medical information populated in graph template box to the IP address, and selection of the communication mode selectable option for e-mailing causes the computing device to send the document template having the medical information populated in graph template box to the e-mail address.

16. The system of claim 12, wherein the plurality of instructions of the software program further includes instructions that when interpreted by the processor cause the computing device and the display to cooperate to:
adjust, upon selection of the graph template box, the size of the graph template box.

17. The system of claim 16, wherein the graph template box includes a plurality of x-axis increment indicators and a plurality of y-axis increment indicators and the plurality of instructions of the software program further includes instructions that when interpreted by the processor cause the computing device and the display to cooperate to:
adjust at least one of the plurality of x-axis increment indicators and the plurality of y-axis increment indicators when the size of the graph template box is adjusted following populating the graph template box with a graph of the medical information relating to the selected one of the patient group and the individual patient.

18. The system of claim 11, wherein the plurality of instructions of the software program further includes instructions that when interpreted by the processor cause the computing device and the display to cooperate to:
display, upon dragging and dropping the graph icon from the content area into the template area, a graph content menu below the graph template box.

19. The system of claim 11, wherein the plurality of instructions of the software program further includes instructions that when interpreted by the processor cause the computing device and the display to cooperate to:
display, upon selection of the graph template box, a graph content menu.

20. The system of claim 12, wherein the plurality of instructions of the software program further includes instructions that when interpreted by the processor cause the computing device and the display to cooperate to:
display, upon dragging and dropping the graph icon from the content area into the template area, a statistics selectable option below the graph template box.

21. The system of claim 20, wherein the plurality of instructions of the software program further includes instructions that when interpreted by the processor cause the computing device and the display to cooperate to:
display, upon selection of the statistics selectable option, statistical data relating to medical information of one of the patient group and the individual patient populated in the graph template box.

* * * * *